(12) United States Patent
Min

(10) Patent No.: US 7,787,951 B1
(45) Date of Patent: Aug. 31, 2010

(54) SYSTEM AND METHOD FOR DETERMINING OPTIMAL STIMULATION SITES BASED ON ECG INFORMATION

(75) Inventor: Xiaoyi Min, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 1156 days.

(21) Appl. No.: 11/416,922

(22) Filed: May 2, 2006

Related U.S. Application Data

(63) Continuation-in-part of application No. 10/745,841, filed on Dec. 24, 2003, now abandoned.

(51) Int. Cl.
*A61N 1/00* (2006.01)

(52) U.S. Cl. ..................................................... 607/17

(58) Field of Classification Search .............. 600/382, 600/424, 434, 459, 508, 515; 607/5, 17, 607/18, 45, 96, 9; 705/2
See application file for complete search history.

(56) References Cited

U.S. PATENT DOCUMENTS

| | | | | |
|---|---|---|---|---|
| 4,402,323 A | | 9/1983 | White | 128/642 |
| 4,777,955 A | | 10/1988 | Brayton et al. | 128/642 |
| 4,787,389 A | | 11/1988 | Tarjan | 128/419 PG |
| 5,331,960 A | * | 7/1994 | Krenzke | 600/382 |
| 5,334,220 A | | 8/1994 | Sholder | 607/9 |
| 5,464,435 A | | 11/1995 | Neumann | 607/9 |
| 5,485,849 A | | 1/1996 | Panescu et al. | 128/699 |
| 5,552,645 A | | 9/1996 | Weng | 307/117 |
| 5,683,429 A | | 11/1997 | Mehra | 602/14 |
| 5,687,737 A | | 11/1997 | Branham et al. | 128/710 |
| 5,876,336 A | | 3/1999 | Swanson | 600/374 |
| 6,128,535 A | | 10/2000 | Maarse | 607/28 |
| 6,141,588 A | | 10/2000 | Cox et al. | 607/9 |
| 6,205,357 B1 | | 3/2001 | Ideker et al. | 607/14 |
| 6,226,542 B1 | | 5/2001 | Reisfeld | 600/407 |
| 6,243,603 B1 | | 6/2001 | Ideker et al. | 607/5 |
| 6,246,898 B1 | | 6/2001 | Vesely et al. | 600/424 |
| 6,301,496 B1 | | 10/2001 | Reisfeld | 600/407 |
| 6,330,476 B1 | | 12/2001 | Ben-Haim et al. | 607/9 |
| 6,358,214 B1 | * | 3/2002 | Tereschouk | 600/508 |
| 6,377,856 B1 | | 4/2002 | Carson | 607/122 |
| 6,456,867 B2 | | 9/2002 | Reisfeld | 600/407 |
| 6,484,118 B1 | | 11/2002 | Govari | 702/150 |
| 6,625,482 B1 | | 9/2003 | Panescu et al. | 600/424 |

(Continued)

FOREIGN PATENT DOCUMENTS

WO    WO 99/06112    11/1999

OTHER PUBLICATIONS

Hein J.J. Wellens, MD et al., "The Electrocardiogram 102 Years After Einthoven," *Circulation*, Feb. 2004; vol. 109, No. 5, pp. 562-564.

(Continued)

*Primary Examiner*—George Manuel
*Assistant Examiner*—Robert N Wieland

(57) ABSTRACT

An exemplary method includes providing surface ECG information acquired using a multi-lead ECG system, providing geometric information acquired using a magnetic resonance imagine system, X-ray imaging system or an ultrasound system and determining one or more stimulation sites for stimulation of the left ventricle based at least in part on the ECG information and the geometric information. Various other exemplary methods, devices, systems, etc., are also disclosed.

20 Claims, 18 Drawing Sheets

U.S. PATENT DOCUMENTS

| | | | |
|---|---|---|---|
| 6,650,927 B1 | 11/2003 | Keidar | 600/424 |
| 6,766,189 B2 | 7/2004 | Yu et al. | 600/510 |
| 6,885,889 B2 | 4/2005 | Chinchoy | 607/9 |
| 6,915,149 B2 | 7/2005 | Ben-Haim | 600/374 |
| 7,398,116 B2 * | 7/2008 | Edwards | 600/424 |
| 2002/0087089 A1 | 7/2002 | Ben-Haim | 600/509 |
| 2002/0143264 A1 | 10/2002 | Ding et al. | 600/510 |
| 2002/0161307 A1 | 10/2002 | Yu et al. | 600/509 |
| 2002/0169484 A1 | 11/2002 | Mathis et al. | 607/9 |
| 2003/0050670 A1 | 3/2003 | Spinelli et al. | 607/9 |
| 2003/0105495 A1 | 6/2003 | Yu et al. | 607/17 |
| 2004/0097806 A1 * | 5/2004 | Hunter et al. | 600/434 |
| 2004/0102812 A1 * | 5/2004 | Yonce et al. | 607/9 |
| 2004/0162496 A1 | 8/2004 | Yu et al. | 600/510 |
| 2004/0215245 A1 * | 10/2004 | Stahmann et al. | 607/5 |
| 2005/0090870 A1 | 4/2005 | Hine et al. | 607/17 |

OTHER PUBLICATIONS

Hans Erik Bøtker, MD, PhD., et al., "Electromechanical Mapping for Detection of Myocardial Viability in Patients with ischemia Cardiomyopathy," *Circulation*, Mar. 2001; vol. 103, No. 12, pp. 1631-1637.

Bruce Hopenfeld et al., "The Effect of Conductivity on ST-Segment Epicardial Potentials Arising from Subendocardial Ischemia," *Annals of Biomedical Eng.*, Jun. 2005; vol. 33, No. 6, pp. 751-763.

* cited by examiner

Exemplary Seven Lead Arrangement
900

Exemplary Coordinate System 940

Exemplary Scenario 1200

SYSTEM AND METHOD FOR DETERMINING OPTIMAL STIMULATION SITES BASED ON ECG INFORMATION

CROSS-REFERENCE TO RELATED APPLICATIONS

This application is a continuation-in-part of co-pending U.S. patent application Ser. No. 10/745,841, filed Dec. 24, 2003, entitled "System and Method for Determining Optimal Pacing Sites Based on Myocardial Activation Times".

FIELD OF THE INVENTION

The invention relates generally to implantable cardiac stimulation systems for use in pacing the heart and in particular to techniques for determining optimal locations for positioning one or more electrodes for use primarily in heart failure patients.

BACKGROUND

Heart failure is one of the most widespread and devastating cardiac afflictions, currently affecting approximately 15 million people worldwide, including over 5 million in the United States. In the U.S., approximately 450,000 new patients are diagnosed with heart failure each year and the majority dies within five years of diagnosis. One factor that contributes to heart failure is asynchronous activation of the ventricles such that the mechanical contraction is not coordinated effectively thus compromising cardiac function. As a result, the pumping ability of the heart is diminished and the patient experiences shortness of breath, fatigue, swelling, and other debilitating symptoms. The weakened heart is also susceptible to potentially lethal ventricular tachyarrhythmias. A decrease in cardiac function can result in a progression of heart failure. In many cases, pacing control parameters of the pacemaker or implantable cardioverter defibrillator (ICD) can be adjusted to help improve cardiac function and reduce the degree of heart failure effectively reducing symptoms and improving the quality of life.

One particularly promising technique for reducing the risk of heart failure is cardiac resynchronization therapy (CRT), which seeks to normalize asynchronous cardiac electrical activation and the resultant asynchronous contractions by delivering synchronized pacing stimulus to both ventricles using pacemakers or implantable cardioverter defibrillators (ICDs) equipped with biventricular pacing capability. The stimulus is synchronized so as to help improve overall cardiac function. This may have the additional beneficial effect of reducing the susceptibility to life-threatening tachyarrhythmias.

While CRT is promising and has helped many patients, some CRT patients have benefited less than others. This has caused the medical community to focus more intensely on the initial question, given a particular patient, is CRT appropriate? As a consequence, various tests and decision processes have emerged to aid in determining whether a patient will respond to CRT. Patients that are likely to respond or do respond have been referred to as "responders". However, the class of actual responders has been confined by regulatory, device and procedural concerns or capabilities. For example, limitations exist as to actual locations considered or approved for positioning a left ventricular stimulation electrode. Thus, an appropriate inquiry is whether the likelihood of a patient responding to CRT depends on the selected stimulation site or sites?

As described herein, surface ECG information is used, optionally in conjunction with other information, to determine one or more stimulation sites for CRT or stimulation based cardiac therapy. Such techniques can help assess a patient's likelihood of responding to therapy prior to implantation of a cardiac therapy device.

SUMMARY

An exemplary method includes providing surface ECG information acquired using a multi-lead ECG system, providing geometric information acquired using a magnetic resonance imagine system, X-ray imaging system or an ultrasound system and determining one or more stimulation sites for stimulation of the left ventricle based at least in part on the ECG information and the geometric information. Various other exemplary methods, devices, systems, etc., are also disclosed.

BRIEF DESCRIPTION OF THE DRAWINGS

The above and further features, advantages and benefits of the present invention will be apparent upon consideration of the present description taken in conjunction with the accompanying drawings, in which.

DETAILED DESCRIPTION

The following description includes the best mode presently contemplated for practicing the invention. This description is not to be taken in a limiting sense but is made merely to describe general principles of the invention. The scope of the invention should be ascertained with reference to the issued claims. In the description that follows, like numerals or reference designators will be used to refer to like parts or elements throughout.

Overview of Technique for Identifying Optimal Pacing Location

Figure 1:
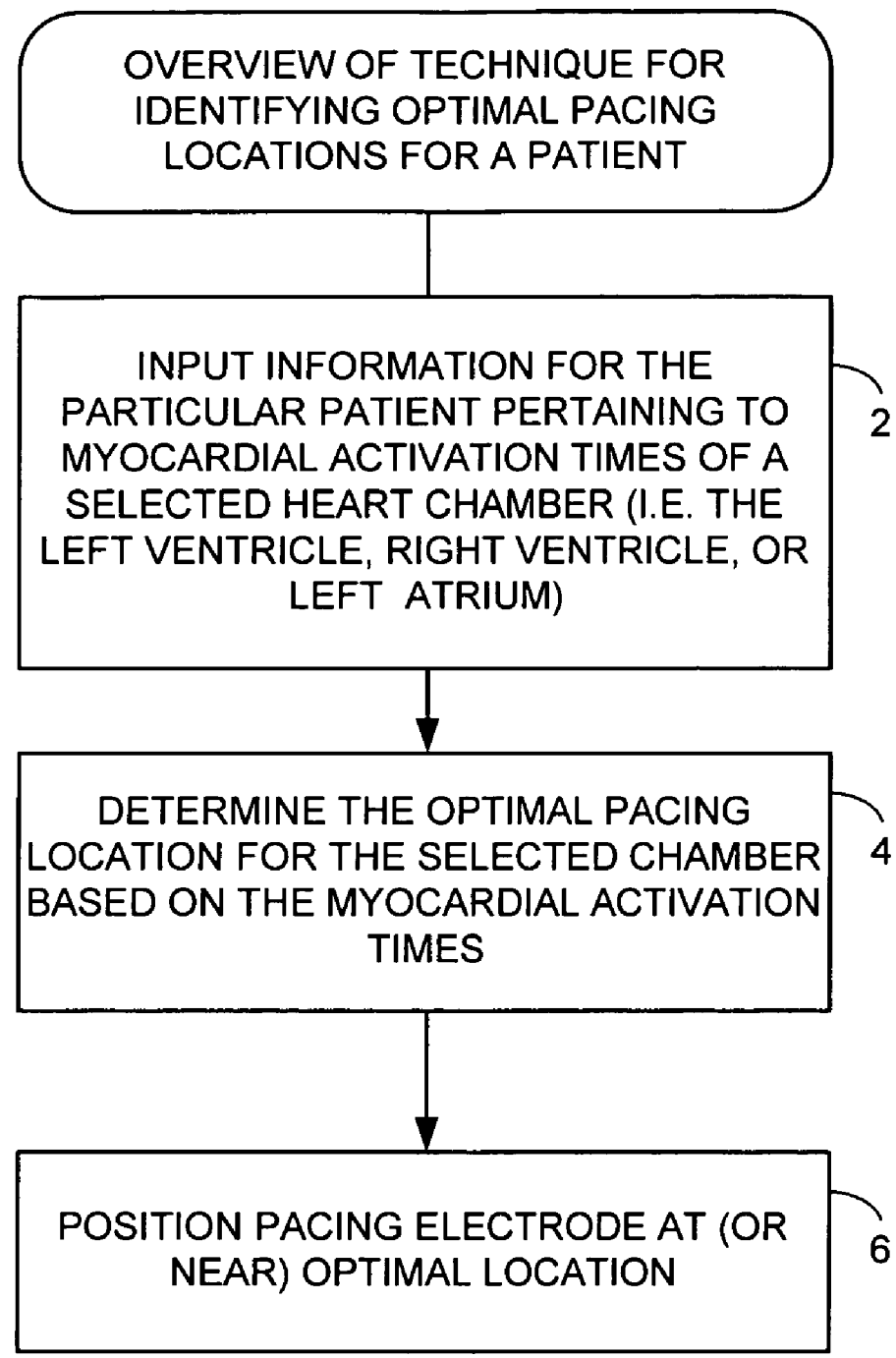
FIG. 1 is a flow chart providing an overview of an exemplary technique provided in accordance with the invention for identifying optimal locations for positioning the pacing electrodes based on myocardial activation times.

FIG. 1 provides an overview of the technique identifying optimal or preferred pacing locations within the heart of a particular patient. Other techniques are described further below, for example, with respect to FIGS. 10-18. Briefly, at step 2, information is input for the particular patient pertaining to be myocardial activation times within a cardiac chamber where a pacing electrode is to be implanted (typically the left ventricle or the right ventricle.) Then, at step 4, the optimal pacing location for that chamber is determined based upon the myocardial activation times. Preferably, the location that is the last electrically activated site within a given chamber is identified as being the optimal or preferred pacing location. For example, the last site within the left ventricular myocardium to depolarize during a ventricular contraction represents the optimal pacing location within the left ventricle. Thereafter, at step 6, a pacing electrode is implanted at or near the optimal location for use in delivering pacing therapy. The technique is perhaps most advantageously applied to identify optimal pacing locations in the ventricles for use in delivering CRT but is applicable to other circumstances as well Examples are described below for both master/satellite pacing systems as well as biventricular single device systems.

As noted above in the Summary, the last activated site within the myocardium of a given chamber is believed to be the optimal site for pacing that chamber because it corresponds to portions of the myocardium that would otherwise contract last in response to intrinsic pacing pulses and hence which most significantly contribute to uneven contraction of the chamber. By delivering pacing pulses directly at that location, adjacent portions of the myocardium can be caused to contract sooner thus improving the uniformity of chamber contraction and thereby improving stroke volume from that chamber and hence improving overall cardiac function. The optimal location detection technique is particularly effective for use in identifying pacing sites in the left or right ventricles but is also applicable to identifying pacing sites in the atria as well.

Overview of Master/Satellite Pacing System

Figure 2:
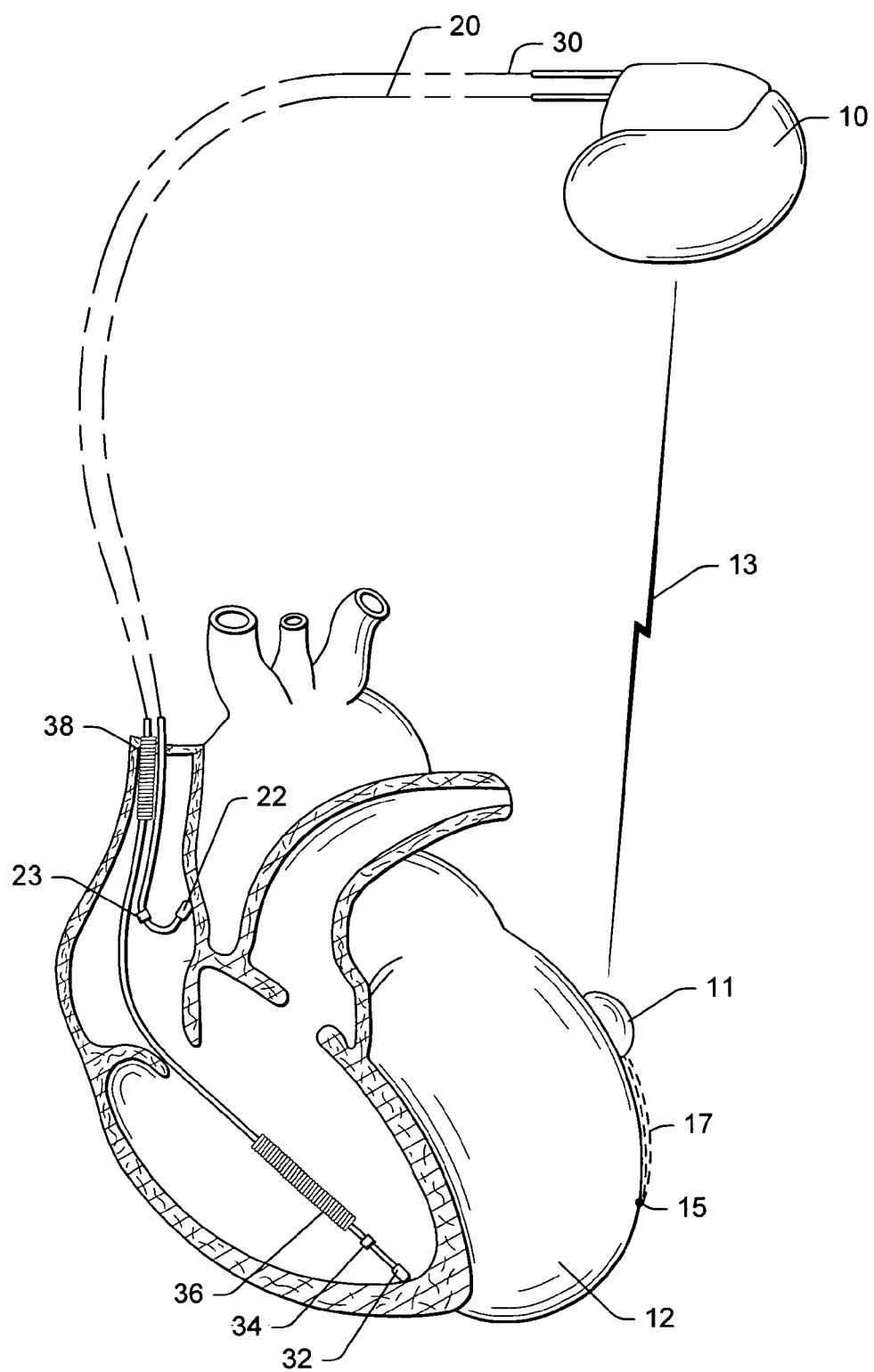
FIG. 2 illustrates an exemplary implantable master/satellite cardiac stimulation system having a master pacing device for delivering stimulation therapy to the right atria and the right ventricle via endocardial electrodes and a satellite pacing device for delivering stimulation therapy to the left ventricle via an epicardial electrode.

FIG. 2 illustrates a master pacing device 10 in electrical communication with a heart 12 by way of three leads 20 and 30 suitable for delivering multi-chamber stimulation and shock therapy. To sense atrial cardiac signals and to provide right atrial chamber stimulation therapy, the master pacing device is coupled to an implantable right atrial lead 20 having at least an atrial tip electrode 22, which typically is implanted in the right atrial appendage. The master pacing device is also shown in electrical communication with the heart by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart so as to place right ventricular tip electrode 32 in the right ventricular apex so that RV coil electrode 36 will be positioned in the right ventricle and SVC coil electrode 38 will be positioned in the superior vena cava. Accordingly, right ventricular lead 30 is capable of receiving cardiac signals and delivering stimulation in the form of pacing and shock therapy to the right ventricle.

FIG. 2 also illustrates a satellite pacing device 11. The satellite pacing device is mounted on the left side of the heart, particularly to the epicardium of the left ventricle. The satellite pacing device can be mounted, for example, using a thoracoscopic procedure during implant of the master pacing device. The satellite pacing device communicates with the master pacing device using wireless communication technologies, such as high frequency modulation, as represented by transmission link 13. The satellite pacing device delivers pacing pulses to the epicardium of the left ventricular via an electrode 15 coupled to the satellite device via lead 17.

The master/satellite system is especially advantageous for use in performing CRT wherein pacing pulses with carefully chosen time delays are delivered to the right ventricle via endocardial lead 30 under control of the master device 10 and to the left ventricle via epicardial electrode 15 under control of the satellite device 11. An example of a master/satellite system, which may be adapted for use in performing CRT, is described in U.S. patent application Ser. No. 10/408,198, entitled "Implantable Cardiac System with Master Pacing Unit and Satellite Pacing Unit", filed Apr. 3, 2003, and is fully incorporated by reference herein.

Figure 3:
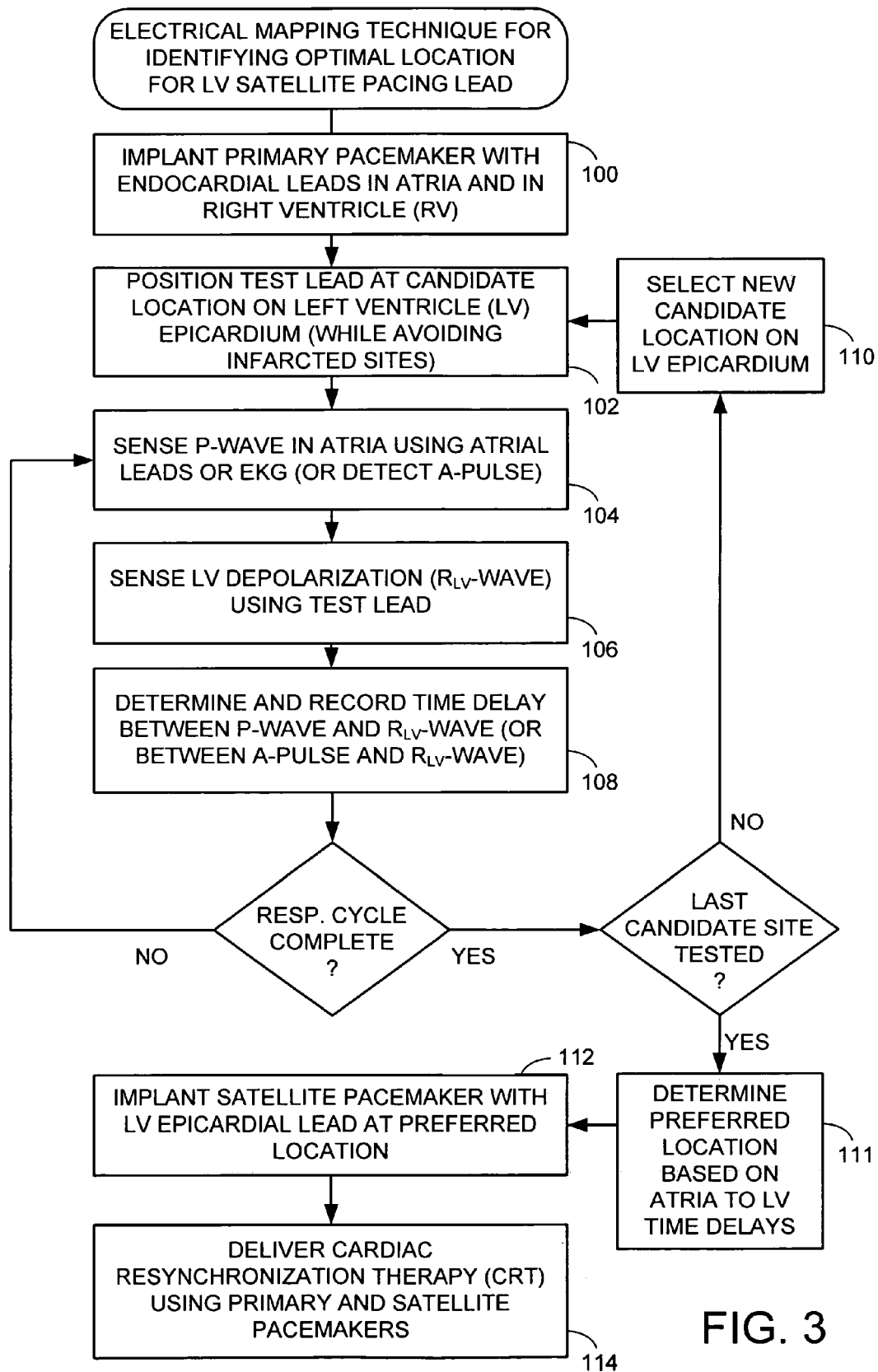
FIG. 3 is a flow chart illustrating an exemplary electrical mapping technique for identifying the optimal location for positioning the epicardial electrode of FIG. 2 based on atrial to LV conduction delays.

Exemplary Electrical Mapping Technique for Identifying Optimal LV Epicardial Pacing Location Based on Time Delays from Atria FIG. 3 illustrates an exemplary electrical mapping technique. Other techniques are described further below. The technique of FIG. 3 pertains to identifying the optimal location for positioning pacing electrode 15 of left ventricular satellite pacer 11 of FIG. 2 based on atrial to left ventricular propagation time delays. Initially, at step 100, the primary pacemaker is implanted within the patient and leads are implanted in the right atrium and the right ventricle, i.e. leads 20 and 30 of FIG. 2 are implanted. Then, at step 102, a test electrode is positioned at a candidate location on the left ventricular epicardium, such as somewhere in the lateral, anterior, posterior and apical regions of the let ventricle. Note that infarcted sites are avoided since such sites are not likely to respond to pacing stimulation. Infarcted sites may be identified using otherwise conventional techniques. (An exemplary technique for identifying infarcted sites based on an analysis of the morphology of evoked response (ER) is discussed below in connection with FIG. 9.) The test electrode may be electrode 15 of the satellite pacer of FIG. 2 or an electrode within a separate sensing probe. For example, the sensing probe may be: a stand alone mapping catheter having either a unipolar or a bipolar lead; a lead introducer with either a unipolar or bipolar lead at its distal end; or an epicardial lead prior to lead fixation. If a mapping catheter is employed as the test electrode, any of a variety of designs can be used. U.S. Pat. No. 4,402,323 to White, entitled "Disposable Electrophysiological Exploring Electrode Needle", describes an epicardial lead with disposable mapping attachment at its distal end. In any case, at step 104, an atrial electrical event is sensed either by a surface ECG or by the master device using tip and ring electrodes implanted within the right atrium. The atrial event may be either an intrinsic depolarization (i.e. P-wave) or a paced event (i.e. an A-pulse). At step 106, the resulting ventricular depolarization (i.e. $R_{LV}$-wave) is sensed in the left ventricular epicardium using the test electrode.

At step 108, the time delay between atrial activation and the resulting LV activation is detected and recorded. In other words, the time delay from detection of the peak of the P-wave (or A-pulse) within the right atrium and the detection of the peak of the resulting $R_{LV}$-wave within the left ventricle is calculated (i.e. $PR_{LV}$ or $AR_{LV}$). This represents the conduction time between the right atrium and the candidate location. This calculation is preferably performed by an external programmer device (shown in FIG. 17) based on data transmitted thereto. Preferably, conduction delays for the number of beats corresponding to at least one respiration cycle are detected and averaged within steps 104-108. In other words, if there are twenty heartbeats in one respiration cycle, steps 104-108 are repeated twenty times. The number of beats needed to cover one respiration cycle may be calculated based on heart rate and respiration rate.

The test electrode is then moved to a new location at step 110, another atrial event is detected, and the propagation time delay between the right atrium and the new location on the left ventricular epicardium is detected and stored. This process is repeated dozens of times while moving the test electrode around the left ventricular epicardium until all of the candidate locations have been tested. Then, at step 111, the preferred or optimal location is determined based on the various right atria (RA) to LV time delays. This may be performed simply be selecting the location having the longest time based on data recorded at step 108. In a technique describe below in connection with FIG. 9, capture thresholds may also be taken into account to ensure that a location is not chosen that will require to high of a pacing pulse magnitude.

Once the optimal or preferred location is identified, the satellite pacemaker is then implanted, at step 112, with its epicardial electrode positioned at the location identified as providing the longest time delay. If desired, prior to the actual mounting of the epicardial pacing electrode, the effectiveness of the optimal location may be verified by applying pacing pulses using the electrode while measuring cardiac function. Then, beginning at step 114, the master pacemaker and the satellite pacemaker are controlled to coordinate the delivery of CRT (or other appropriate therapy) by selectively applying ventricular pacing pulses to the right and left ventricles using the right ventricular lead of the master pacemaker and the epicardial lead of the satellite pacemaker (as well as the atrial leads of the master pacemaker.)

Note that, once the longest time delay is found at step 111, the location may then be marked with a contrast agent so that the location can be easily identified later for mounting the epicardial electrode. Contrast agents for use in marking myocardial tissue are well known in the art. Alternatively, the best location within each of a set of various regions of the left ventricular can be separately marked for later selection. In still other implementations, the locations are not marked. Instead, when it comes time to implant the satellite pacemaker, the satellite pacemaker is mounted within a region know to contain the best pacing locations and then the specific location for mounting pacing electrode 15 is re-identified within that region by again performing steps 102-111.

As noted, the actual determination of the optimal location performed at step 111 is preferably performed by an external programmer (or other external device). Otherwise conventional software programming techniques may be used to develop software for averaging the delay times recorded at each candidate location, for determining the optimal location from the averaged values, and for displaying the results on the external programmer for view by the physician or other medical personnel. Graphics software may be employed for displaying a digital map or model of the heart of the patient along with an indication of the optimal pacing location so that the location can be easily visualized. In some cases, the physician may choose to mount the epicardial electrode at a location that is not necessarily optimal in terms of delay times but that has other countervailing advantages. Accordingly, the relative conduction delay times of the other locations tested are also preferably displayed for comparison purposes. The map or model of the heart is preferably a 3-D representation, which may be based on the actual heart of the patient and generated based upon CAT scans or other 3-D imaging techniques. Information pertaining to conduction pathways may be acquired and analyzed in any of a variety of manners and electrode configurations and/or stimulation parameters selected based at least in part on pathway information. Exemplary 3-D cardiac imaging techniques are set forth in U.S. Pat. No. 5,687,737 to Branham et al., entitled "Computerized Three-Dimensional Cardiac Mapping With Interactive Visual Displays." See also U.S. Pat. No. 6,625,482 to Panescu et al., entitled "Graphical User Interface for Use with Multiple Electrode Catheters". The aforementioned patent application to Ben-Haim also discusses techniques for generating maps of the heart. Alternatively, the 3-D representation may be a generic representation of a human heart. In either case, otherwise conventional techniques may be employed for digitizing the various locations of the test electrode so that the locations can be displayed in conjunction with the representation of the heart. Exemplary techniques for computing electrode locations in 3-D coordinates are discussed in U.S. Pat. No. 5,485,849 to Panescu et al. See also U.S. Pat. No. 6,246,898 to Vesely et al., entitled "Method for Carrying out a Medical Procedure Using a Three-Dimensional Tracking and Imaging System." An added advantage of recording a 3-D representation of the heart along with the conduction times at various locations on the epicardium is that, if the electrode needs to be repositioned later, the entire process need not be repeated. Rather the physician can instead just review the delay times as displayed in conjunction with the model of the heart and select an alternate epicardial pacing location.

Although described with reference to an LV epicardial electrode, the techniques of FIG. 3 are equally applicable to identifying the optimal location for an RV satellite pacer epicardial electrode. Indeed, optimal locations for both LV and RV epicardial pacing may be identified. In one example, the optimal location for the RV epicardium is first determined based on propagation time delays from the atria to the right ventricle then the optimal time delay for the LV epicardium is determined based on propagation time delays from the atria to the left ventricle. Moreover, the techniques may be adapted for identifying optimal locations for atrial epicardial pacing, if such is desired. For example, time delays may be detected between right atrial pacing events (such as A-pulses generated by RA lead 220) and resulting left atrial depolarizations ($P_{LV}$-wave) sensed via a sensing probe positioned on the left atrium epicardium. The time delays are then used to identify the optimal location for a left atrial (LA) epicardial pacing lead. The technique can also be extended to identifying an optimal location for right atrial (RA) epicardial pacing, preferably for use in combination with an endocardial RA pacing lead.

Thus far, techniques for identifying an optimal pacing location for epicardial electrodes have been described. In the next sections, techniques for identifying the optimal location for positioning tip electrodes of an internal pacing leads will be described.

Overview of the Biventricular Single Device Stimulation System

Figure 4:
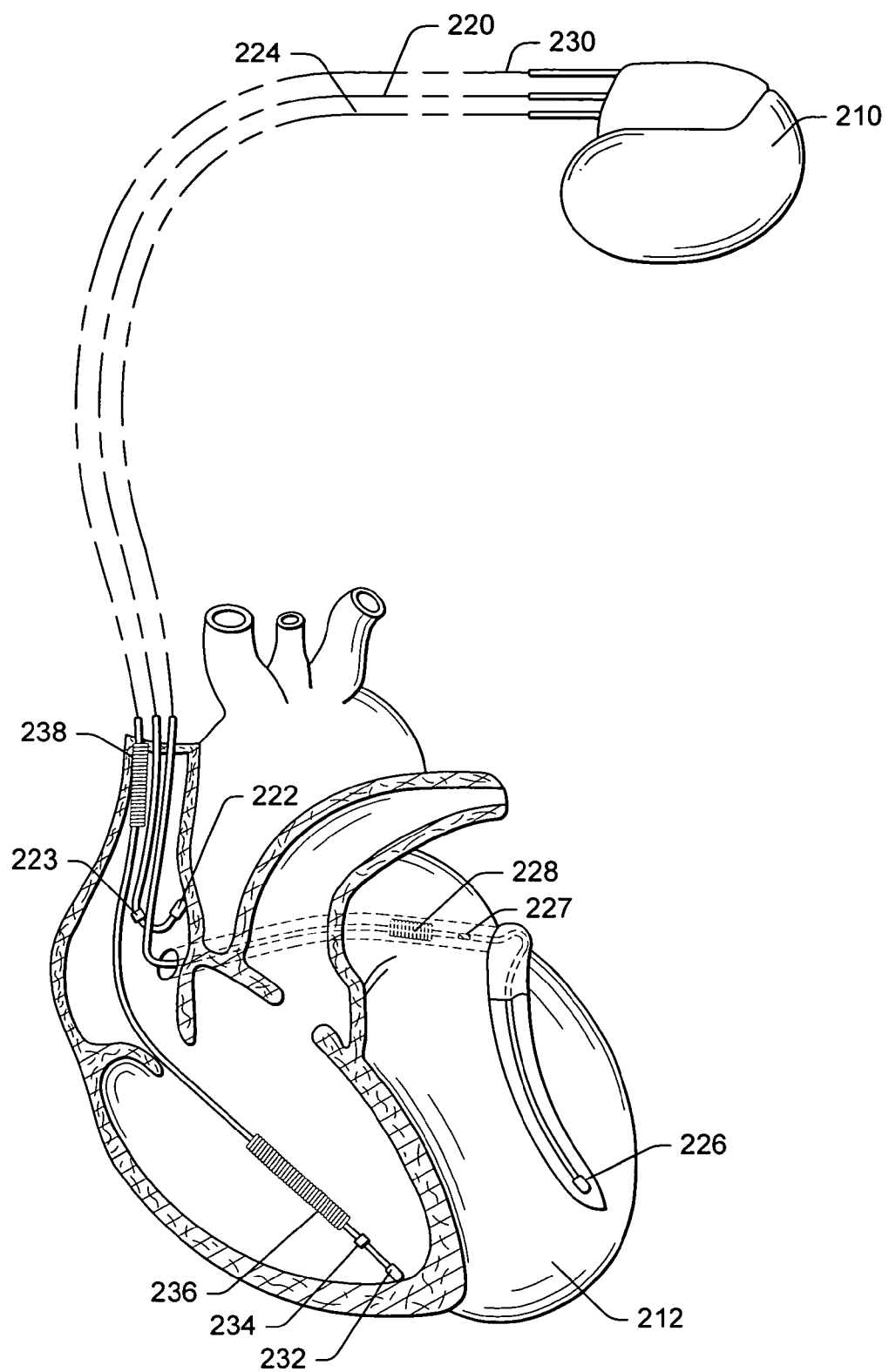
FIG. 4 illustrates an exemplary implantable cardiac stimulation system having a biventricular stimulation device for delivering therapy to all four chambers of the heart via various endocardial electrodes including an LV electrode.

In FIG. 4, a simplified block diagram is shown of a dual-chamber implantable stimulation device 210, which is capable of treating both fast and slow arrhythmias with stimulation therapy, including cardioversion, defibrillation, and pacing stimulation. To provide atrial chamber pacing stimulation and sensing, stimulation device 210 is shown in electrical communication with a heart 212 by way of a left atrial lead 220 having an atrial tip electrode 222 and an atrial ring electrode 223 implanted in the atrial appendage. The stimulation device 210 is also in electrical communication with the heart by way of a right ventricular lead 230 having, in this embodiment, a ventricular tip electrode 232, a right ventricular ring electrode 234, a right ventricular coil electrode 236, and a SVC coil electrode 238. Typically, the right ventricular lead 230 is transvenously inserted into the heart so as to place the RV coil electrode 236 in the right ventricular apex, and the SVC coil electrode 238 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, the stimulation device 210 is coupled to a "coronary sinus" lead 224 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 224 is designed to receive atrial and ventricular cardiac signals and to deliver left ventricular pacing therapy using at least a left ventricular tip electrode 226, left atrial pacing therapy using at least a left atrial ring electrode 227, and shocking therapy using at least a left atrial coil electrode 228. With this configuration, biventricular pacing can be performed. Although only three leads are shown in FIG. 4, it should also be understood that additional stimulation leads (with one or more pacing, sensing and/or shocking electrodes) may be used in order to efficiently and effectively provide pacing stimulation to the left side of the heart or atrial cardioversion and/or defibrillation.

Figure 5:
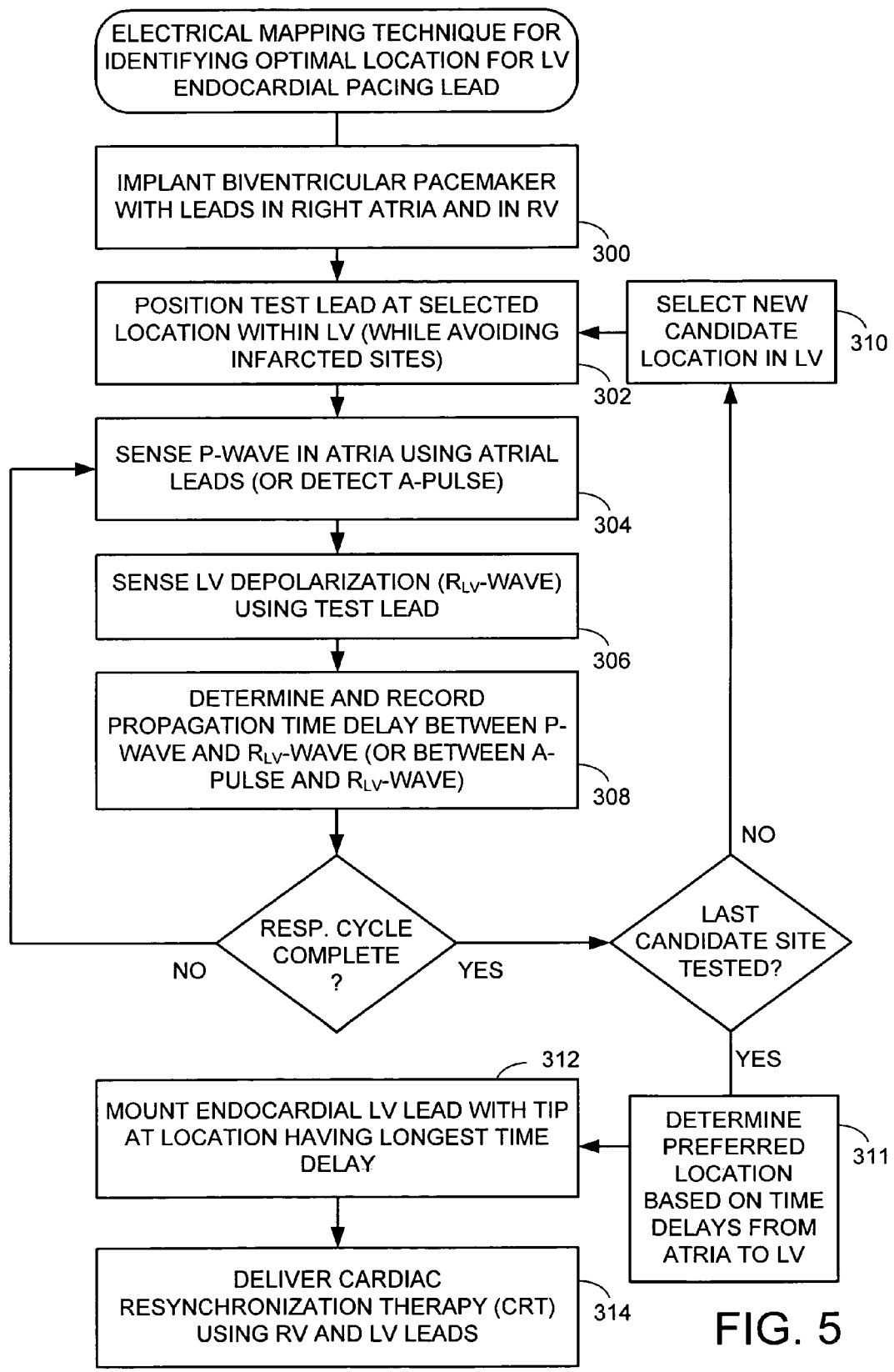
FIG. 5 is a flow chart illustrating an exemplary electrical mapping technique for identifying the optimal location for positioning the LV electrode of FIG. 4 based on atrial to LV conduction delays.
Figure 17:
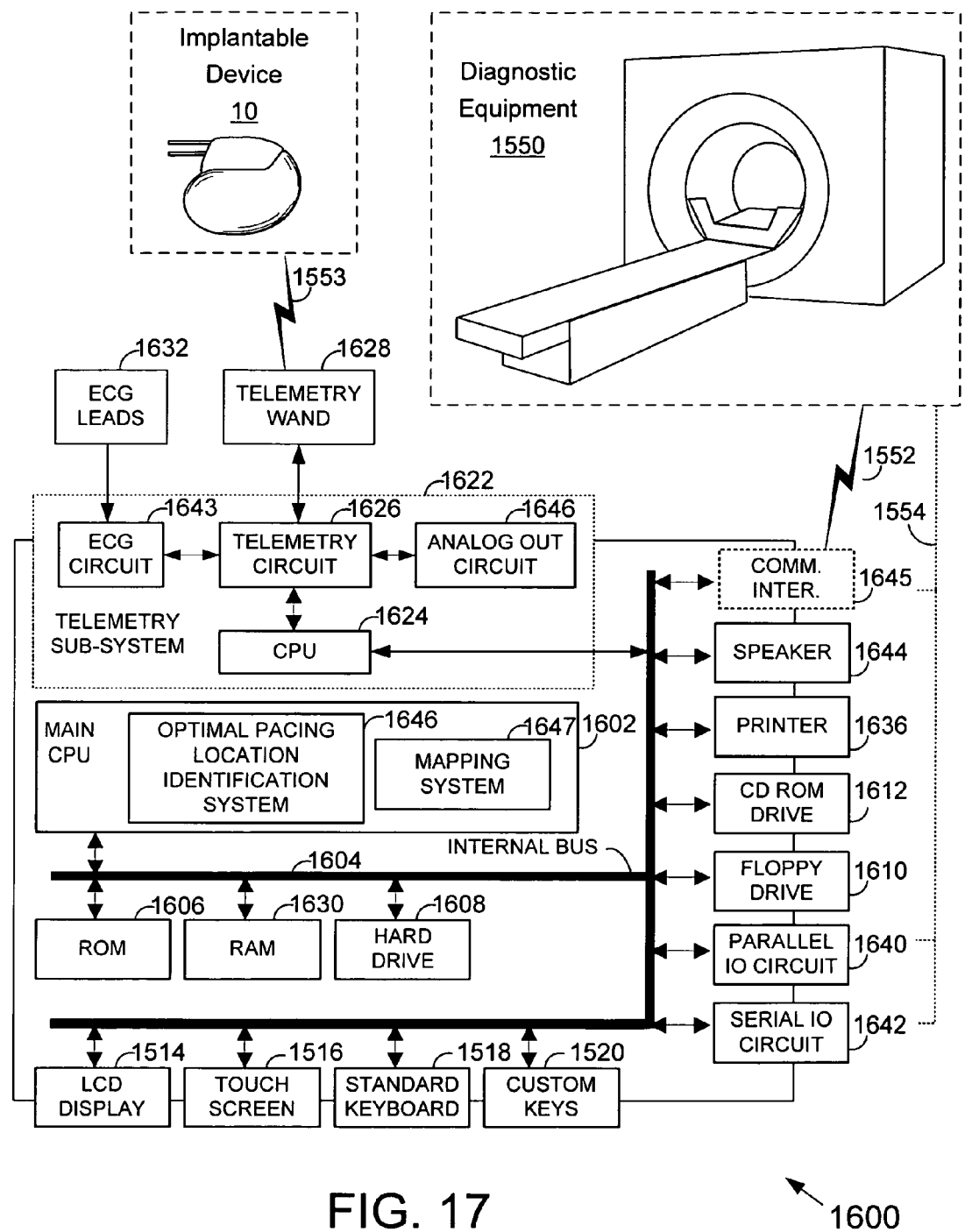
FIG. 17 is a functional block diagram of components of an external programmer device along with an implantable device and diagnostic equipment for use with various techniques described herein.

Exemplary Electrical Mapping Technique for Identifying Optimal LV Endocardial Pacing Location Based on Time Delays from Atria FIG. 5 illustrates an exemplary electrical mapping technique for identifying the optimal location for mounting tip 226 of left the ventricular lead 224 of FIG. 2 based on atrial to ventricular delays. Various other techniques are described further below. Many of the steps of FIG. 5 are similar to those of FIG. 3 and only pertinent differences will be described in detail. Beginning at step 300, a biventricular pacemaker is implanted within the patient with leads 220 and 230 mounted within the atria and in the right ventricle. Beginning at step 302, a sensing probe (or the tip 226 of LV lead 224) is positioned at a candidate location against the left ventricular endocardium. Note that, as before, infarcted sites are avoided. An exemplary endocardial sensing probe for use within the left ventricle is set forth in U.S. Pat. No. 4,777,955 to Brayton et al., entitled "Left Ventricle Mapping Probe." At step 304, an atrial event is sensed by the pacemaker using atrial tip and ring electrodes 222 and 223. As before, the atrial event may be either an intrinsic depolarization (i.e. P-wave) or a paced event (i.e. an A-pulse). At step 306, the resulting LV depolarization ($R_{LV}$-wave) is sensed using the LV lead. The propagation time delay between the atrial event and the LV depolarization is determined at step 308 and this value is recorded, preferably using an external device (FIG. 17). Accordingly, the atrial and ventricular data sensed at steps 304 and 306 is first transmitted to the external programmer. In addition, as in the preceding embodiment, data for the number of beats corresponding to at least one respiration cycle is preferably recorded for the candidate location. Then, a new endocardial location is selected at step 310 and the process is repeated. Once all of the candidate locations have been tested then, at step 311, the preferred or optimal location is determined based on the various RA to LV time delays. A contrast agent may be used to mark the optimal location for subsequent mounting of the tip of lead 230. An endocardial sensing lead with capability for delivering a contrast agent is set forth in U.S. Pat. No. 6,377,856 to Carson, entitled "Device and Method for Implanting Medical Leads". At step 312, the tip of a left ventricular pacing lead is mounted at or near the optimal location. Beginning at step 314, CRT (or other appropriate pacing therapy) is delivered the using the pacemaker via the left and right ventricular leads and the atrial leads.

As with the technique of FIG. 3, any appropriate imaging techniques may be used to display the optimal pacing location in conjunction with a map or model of the heart. To this end, a suitable 3-D location digitizing technique can be used while the tip of the lead is placed at various locations within the heart to allow the location of the tip of the lead to be recorded along with the corresponding time delay value for display along with a 3-D map of the heart (generic or otherwise). A technique for mapping the interior of the left ventricle is discussed in Bøtker et al., "Electromechanical Mapping for Detection of Myocardial Viability in Patients With Ischemic Cardiomyopathy", Circulation 2001; 103:1631-1637.

Although described with reference to an LV lead, the technique of FIG. 5 is equally applicable to identifying the optimal location for tip 232 of RV lead 230 and to identifying optimal locations for both LV and RV endocardial pacing. For example, the optimal location for the RV endocardium is first determined based on propagation time delays from the atria to the right ventricle then the optimal time delay for the LV endocardium is determined based on propagation time delays from the atria to the left ventricle. In addition, the techniques may be adapted for identifying optimal locations for endocardial left atrial pacing. In other words, the technique may be used to identify a location for mounting an endocardial left atrial pacing lead (not specifically shown in FIG. 4.) Time delays may be detected between right atrial pacing events (such as A-pulses generated by RA lead 220) and resulting left atrial depolarizations ($P_{LV}$-wave) sensed via a sensing probe positioned within the left atrium. The time delays are used to identify the optimal location for an RA endocardial pacing lead. The last electrically activated site within the RA endocardium is identified as the preferred location.

In the following, various alternative mapping techniques will be described including techniques exploiting mechanical, rather than electrical, myocardial activation times and techniques that exploit LV to RV delays or RV to LV delays, rather than atrial to ventricular delays. The devices and systems illustrated in FIGS. 2 and 4 may be utilized in connection with the implementing the techniques of the remaining figures as well.

Figure 6:
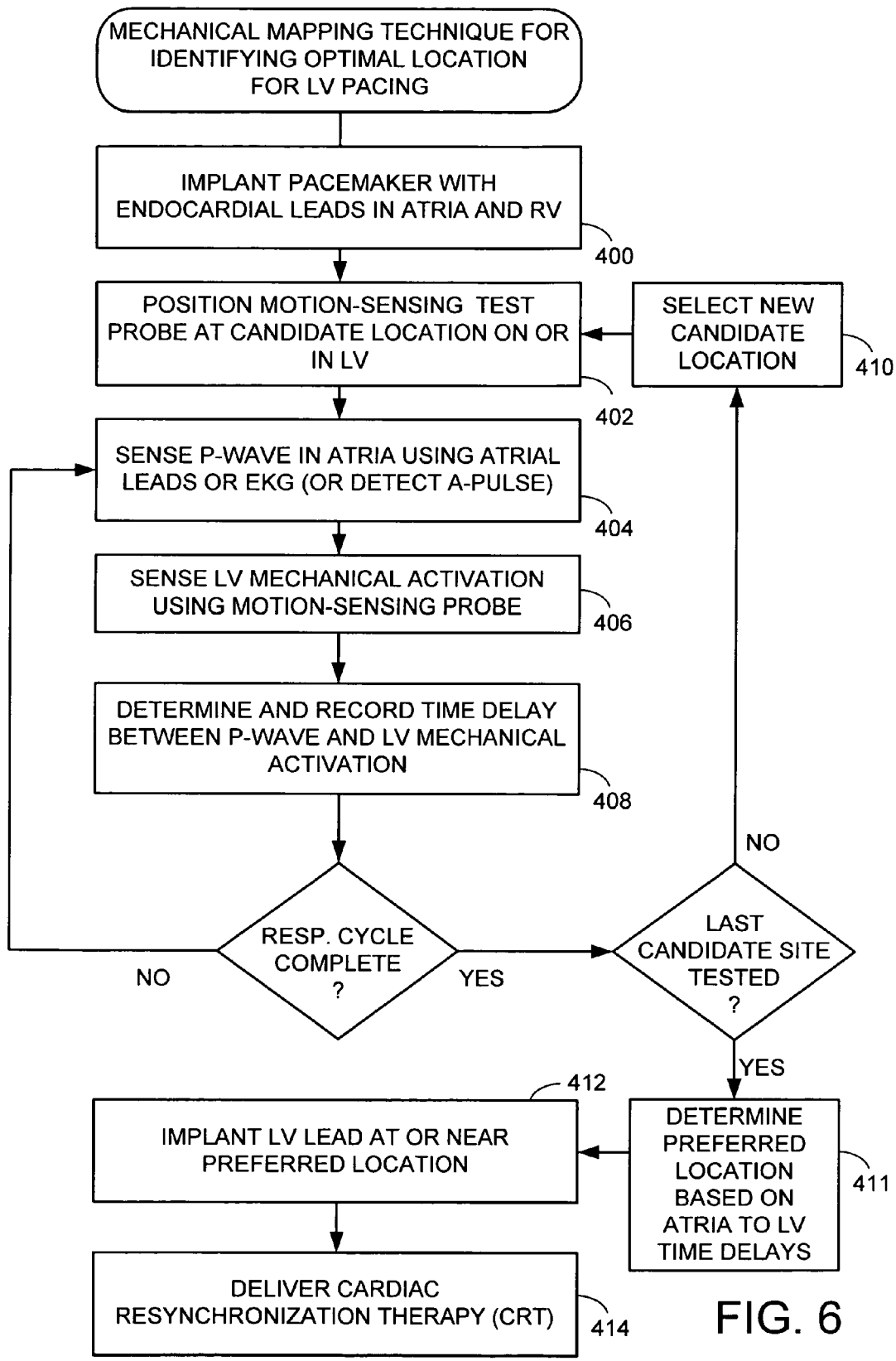
FIG. 6 is a flow chart illustrating an exemplary mechanical mapping technique for identifying the optimal location for positioning an LV electrode based on atrial to LV conduction delays.

Exemplary Mechanical Mapping Technique for Identifying Optimal LV Epicardial Pacing Location Based on Time Delay from Atria FIG. 6 illustrates an exemplary mechanical mapping technique for identifying the optimal location for positioning a pacing electrode based on physical contraction of the myocardium of the heart. Many of the steps of FIG. 6 are similar to those of FIGS. 3 and 5 and only pertinent differences will be described in detail. Beginning at step 400, a master pacer or biventricular pacemaker is implanted within the patient with leads 220 and 230 mounted within the atria and in the right ventricle. Beginning at step 402, a motion-sensing probe is positioned at a candidate location in or on the left ventricular myocardium. The motion-sensing probe may be any probe capable of sensing the physical (or mechanical) contraction of portions of the myocardium of the heart. This is in contrast to an electrical sensing probe for sensing the electrical depolarization of the myocardium. The motion-sensing probe may incorporate both electrical and mechanical components and may, for example, contain an accelerometer or similar motion sensor. Medical probes employing motion-sensing accelerometers are discussed in U.S. Pat. No. 5,552,645 to Weng. Alternatively, an electromagnetic 3D sensor may be employed or a sensor designed to detect longitudinal contraction of myocytes. In any case, if the technique is being performed to identify an epicardial pacing location, then the motion-sensing probe is preferably placed adjacent the LV epicardium. If the technique is being performed to identify an endocardial pacing location, then the motion-sensing probe is preferably placed adjacent an inner wall of the LV. As before, infarcted sites are avoided.

At step 404, an atrial event is sensed by the pacemaker using atrial tip and ring electrodes. As before, the atrial event may be either an intrinsic depolarization (i.e. P-wave) or a paced event (i.e. an A-pulse). At step 406, the resulting contraction of the portion of the myocardium adjacent the probe during LV depolarization is sensed using the motion-sensing probe. The propagation time delay between the atrial event and the mechanical contraction of the adjacent portion of the LV myocardium is determined at step 408 and this value is recorded, preferably using the external device of FIG. 17. Data for the number of beats corresponding to at least one respiration cycle is preferably recorded for the candidate location. Then, a new candidate location is selected at step 410 and the process is repeated. Once all of the candidate locations have been tested then, at step 411, the preferred or optimal location is determined based on the various RA to LV time delays. As before, a contrast agent may be used to mark the optimal location for subsequent mounting of LV electrode. At step 412, the LV pacing electrode is then mounted at or near the optimal location (epicardial or endocardially, as needed). Beginning at step 414, CRT (or other appropriate therapy) is then delivered.

As with the aforementioned techniques, any appropriate imaging techniques may be used to display the optimal pacing location in conjunction with a map or model of the heart. Moreover, although described with reference to an LV lead, the technique of FIG. 6 is equally applicable to identifying the optimal location for an RV electrode or to identifying optimal locations for both LV and RV pacing. In addition, the techniques may be adapted for identifying optimal locations for left atrial pacing. Also, rather than using a motion-sensing probe, the technique of FIG. 6 may instead exploit tissue Doppler imaging techniques wherein the location within a given chamber having the last activation time is identified by examining contraction of various portions of the myocardium of the chamber via Doppler imaging. An example of a Doppler imaging technique is set forth in U.S. Pat. No. 6,650,927 to Keidar, entitled "Rendering of Diagnostic Imaging Data on a Three-Dimensional Map", which his incorporated by reference herein. Also, techniques set forth in the patents referenced above to Branham et al., Panescu et al., Ben-Haim and Vesely et al. may be exploited in connection with detecting and/or mapping the physical contraction of portions of the myocardium of the heart. See also U.S. Pat. No. 6,484,118, entitled "Electromagnetic Position Single Axis System" to Govari; U.S. Pat. No. 6,456,867, entitled "Three-Dimensional Reconstruction of Intrabody Organs" to Reisfeld; 6,301,496, entitled "Vector Mapping of Three-Dimensionally Reconstructed Intrabody Organs and Method of Display" also to Reisfeld; and U.S. Pat. No. 6,226,542, entitled "Three-Dimensional Reconstruction Of Intrabody Organs" also to Reisfeld.

Figure 7:
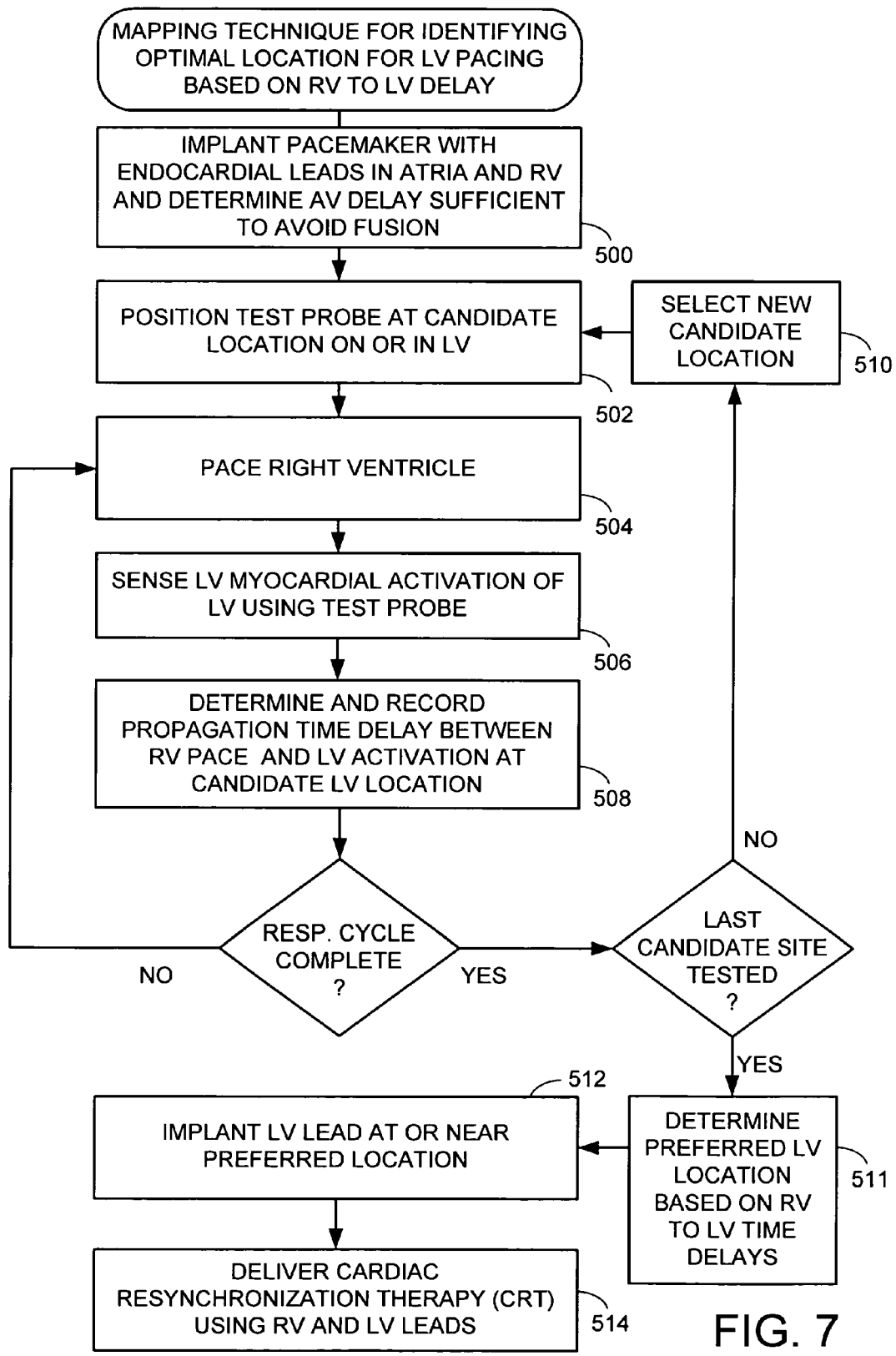
FIG. 7 is a flow chart illustrating an exemplary mapping technique for identifying the optimal location for positioning an LV electrode based on RV to LV conduction delays.

Exemplary Mapping Technique for Identifying Optimal LV Epicardial Pacing Location Based on Time Delay from RV to LV FIG. 7 illustrates an exemplary mapping technique for identifying the optimal location for positing epicardial or endocardial LV pacing leads based on RV to LV time delays. Various other techniques are described further below. The technique of FIG. 7 is in contrast with the foregoing technique that operates based on atrial to ventricular delays. Nevertheless, many of the steps of FIG. 7 are similar to those described above and only pertinent differences will be described in detail. Beginning at step 500, a master pacer or biventricular pacemaker is implanted within the patient with leads 220 and 230 mounted within the atria and in the right ventricle. The lead is the RV is typically mounted in the endocardial apex. In addition, at step 500, an atrioventricular (AV) delay is set to a sufficiently short value to avoid any substantial risk of fusion during RV pacing. In this regard, if the AV delay is to long, then AV conduction from the atria to the ventricles may result in intrinsic depolarization of the ventricles occurring slightly before or contemporaneous with depolarization caused by RV pacing pulses. Techniques for identifying AV delay values sufficient to avoid fusion are discussed in U.S. Pat. No. 5,334, 220 to Sholder, entitled "Dual-Chamber Implantable Pacemaker Having An Adaptive Av Interval That Prevents Ventricular Fusion Beats And Method Of Operating Same", which is incorporated by reference herein.

Beginning at step 502, a motion-sensing or electrical sensing probe is positioned at a candidate location in or on the left ventricular myocardium. If the technique is performed to identify an epicardial pacing location, the probe is preferably placed adjacent the LV epicardium. If the technique is performed to identify an endocardial pacing location, the probe is preferably placed adjacent an inner wall of the LV. As before, infarcted sites are avoided. At step 504, a pacing pulse is delivered to the RV using the RV tip and ring electrodes subject to the aforementioned AV delay. At step 506, the resulting LV depolarization is sensed using either the sensing probe. The propagation time delay between the RV pace and the resulting LV activation is determined at step 508 and this value is recorded using the external device of FIG. 17. Data for the number of beats corresponding to at least one respiration cycle is preferably recorded for the candidate location. A new candidate location is selected at step 510 and the process is repeated. Once all of the candidate locations have been tested then the preferred or optimal location is determined, at step 511, based on the various RV to LV time delays. As before, a contrast agent may be used to mark the optimal location for subsequent mounting of LV electrode. At step 512, the LV pacing electrode is then mounted at or near the optimal location (epicardial or endocardially, as needed). Beginning at step 514, CRT (or other appropriate therapy) is then delivered.

As with the aforementioned techniques, any appropriate imaging technique may be used to display the optimal pacing location in conjunction with a map or model of the heart. Moreover, although described with reference to identifying the optimal location for an LV lead based on RV to LV delays, the technique of FIG. 7 is equally applicable to identifying the optimal location for an RV electrode based on LV to RV delays arising from a fixed LV pacing electrode. Also, rather than using an electrical or a motion-sensing sensing probe, the technique of FIG. 7 may instead exploit tissue Doppler imaging techniques to detect mechanical activation time delays.

Figure 8:
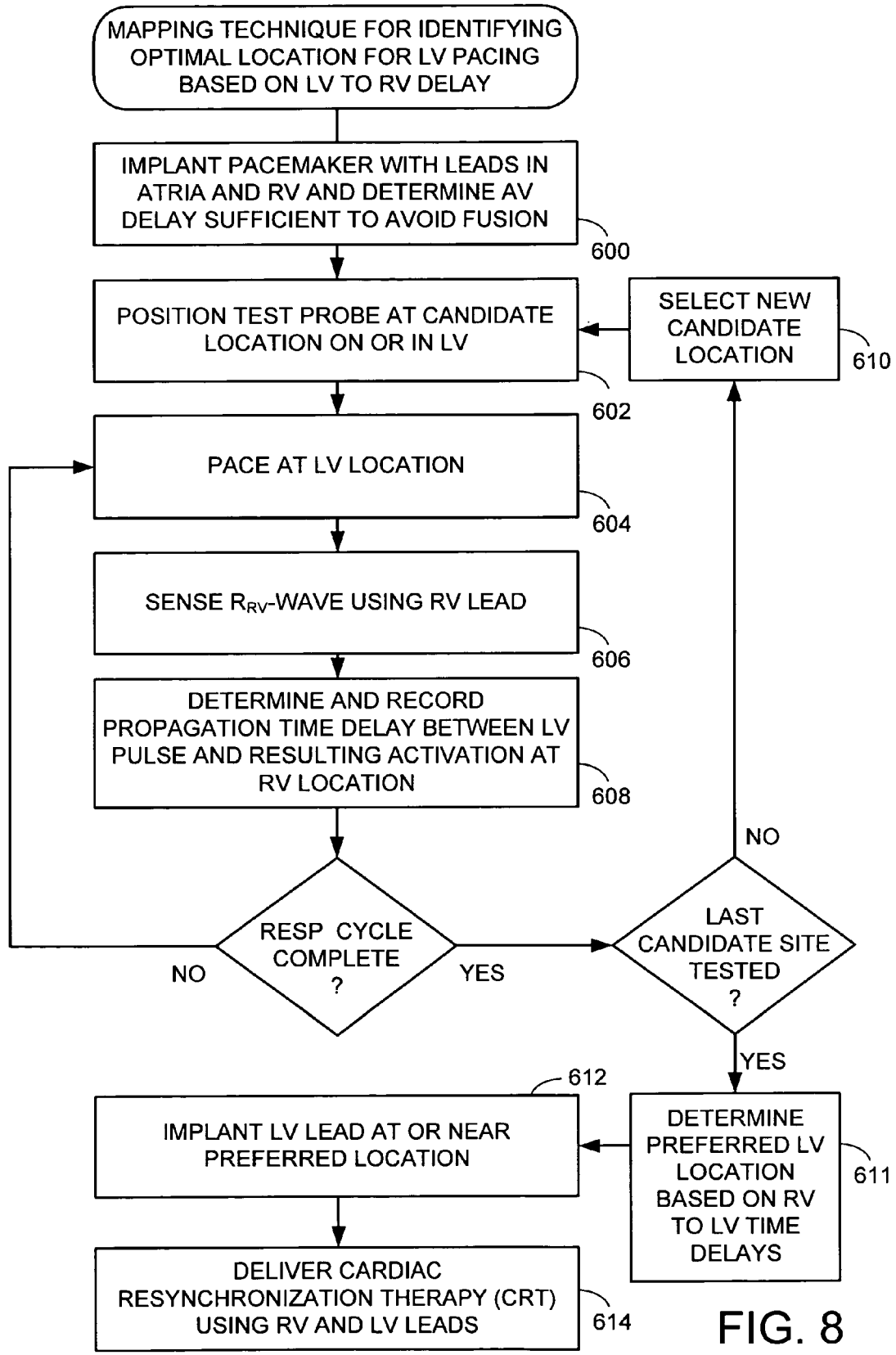
FIG. 8 is a flow chart illustrating an exemplary mapping technique for identifying the optimal location for positioning an LV electrode based on LV to RV conduction delays.

Exemplary Mapping Technique for Identifying Optimal LV Epicardial Pacing Location Based on Time Delay from LV to RV FIG. 8 illustrates an exemplary mapping technique for identifying the optimal location for positing epicardial or endocardial LV pacing leads based on LV to RV time delays triggered by LV pacing. Various other techniques are described further below. With respect to the technique of FIG. 8, a pacing probe is used to apply pacing pulses to the LV. This is in contrast with the foregoing techniques that operate using sensing probes for sensing LV activation. Nevertheless, many of the steps of FIG. 8 are similar to those described above and only pertinent differences will be described in detail. Beginning at step 600, a master pacer or biventricular pacemaker is implanted within the patient with leads 220 and 230 mounted within the atria and in the right ventricle. In addition, at step 600, the AV delay is set to a sufficiently short value to avoid any substantial risk of fusion during LV pacing. Beginning at step 602, an electrical pacing probe is positioned at a candidate location in or on the left ventricular myocardium. A suitable pacing/mapping probe is set forth in the above-referenced patent to White. If the technique is performed to identify an epicardial pacing location, the pacing probe is preferably placed adjacent the LV epicardium. If the technique is performed to identify an endocardial pacing location, the pacing probe is preferably placed adjacent an inner wall of the LV. As before, infarcted sites are avoided.

At step 604, an LV pacing pulse is delivered by an external device using the LV pacing probe based on the AV delay. At step 606, a resulting RV depolarization is sensed using the electrodes mounted in the right ventricle (i.e. electrodes 32 and 34 of FIG. 2 or electrodes 232 and 234 of FIG. 4, depending upon the implementation.) The propagation time delay between the LV pacing pulse and the resulting RV activation is determined at step 608 and this value is recorded using the external device of FIG. 17. Data for the number of beats corresponding to at least one respiration cycle is preferably recorded for the candidate location. A new candidate location is then selected at step 610 and the process is repeated. Once all of the candidate locations have been tested then the preferred or optimal location is determined, at step 611, based on the various LV to RV time delays. As before, a contrast agent may be used to mark the optimal location for subsequent mounting of an LV electrode. At step 612, an LV pacing electrode is then permanently mounted at or near the optimal location (epicardial or endocardially, as needed). If the LV pacing probe is intended to be used as the permanent LV pacing electrode then it may be mounted at the optimal location immediately. In any case, beginning at step 614, CRT or other appropriate therapy is then delivered.

As with the aforementioned techniques, any appropriate imaging techniques may be used to display the optimal pacing location in conjunction with a map or model of the heart. Moreover, although described with reference to identifying the optimal location for an LV lead based on LV to RV delays, the technique of FIG. 8 is equally applicable to identifying the optimal location for an RV electrode based on RV to LV delays triggered by an RV pacing probe and detected by a fixed LV electrode.

Figure 9:
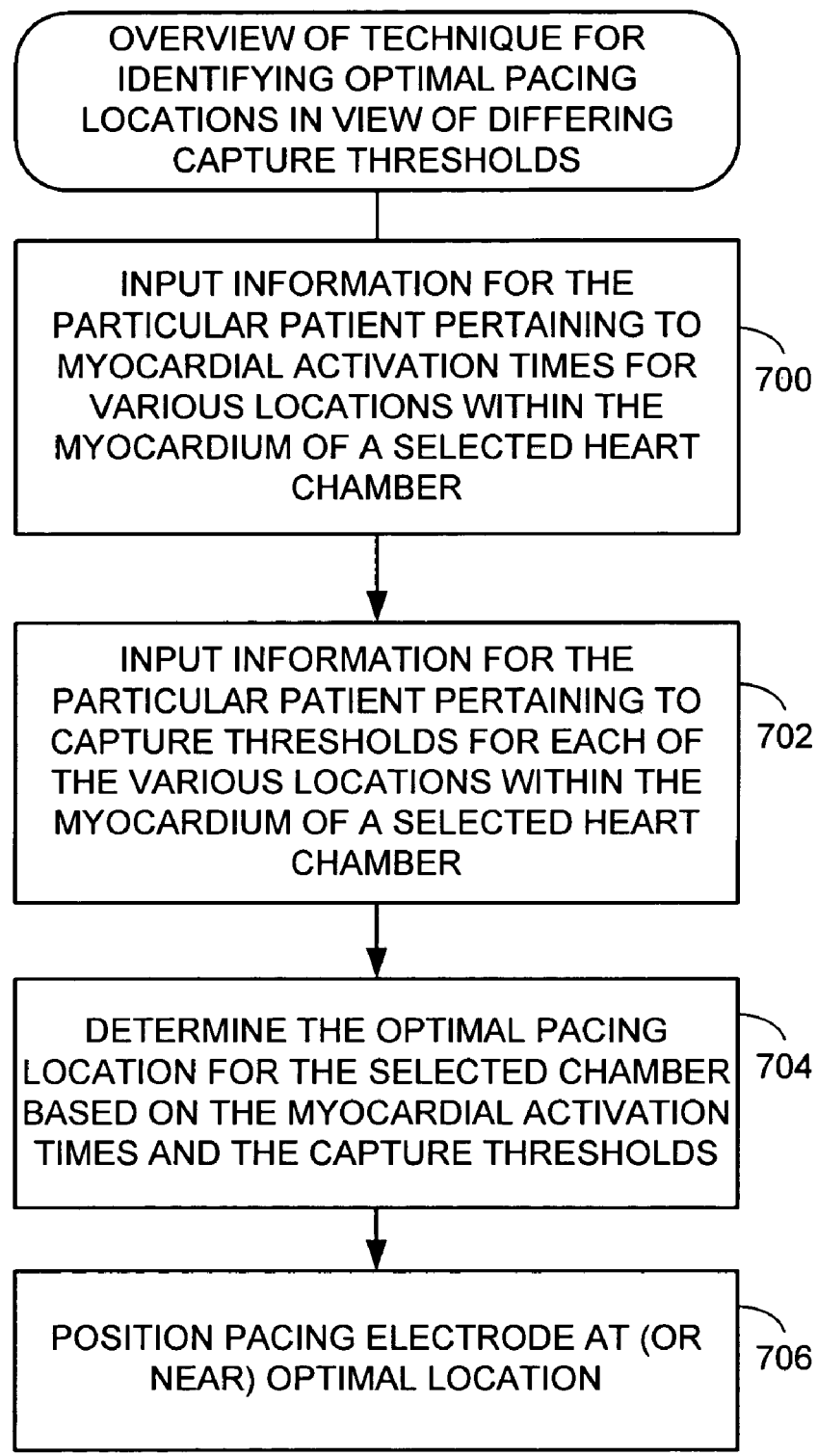
FIG. 9 is a flow chart providing an overview of an exemplary technique, also provided in accordance with the invention, for identifying optimal locations for positioning pacing electrodes based on both myocardial activation delays and capture thresholds.

Overview of Technique for Identifying Optimal Pacing Location while Taking into Account Capture Thresholds FIG. 9 provides an overview of a technique for identifying optimal pacing locations for a particular patient while taking into account capture thresholds. More specifically, the technique of FIG. 9 operates to determine an optimal pacing location based on both the activation time delay and on the capture threshold so as to ensure that a pacing location is not selected that has a capture threshold that is too high and in particular to exclude sites that cannot be electrically activated by a pacing electrode, perhaps because the myocardial tissue at that site was subject to infarction. The technique may be used in conjunction with any of the exemplary techniques described above.

Briefly, at step 700, information is input for the particular patient pertaining to be myocardial activation times for various locations on or within a cardiac chamber where a pacing electrode is to be implanted (such as within the left ventricle). This is performed in accordance with the techniques described above. Additionally, at step 702, information is input pertaining to be capture thresholds for each of the various locations of step 700. This information may be generated using a pacing probe. Then, at step 704, the optimal pacing location is determined based upon both the myocardial activation times and the capture thresholds. In one example, a maximum acceptable capture threshold is specified and then the location having the latest activation time is selected only from among locations with capture thresholds not exceeding the threshold. Thereafter, at step 706, a pacing electrode is implanted at or near the optimal location for use in delivering pacing therapy.

The capture-based technique of FIG. 9 is perhaps most advantageously applied for use in connection with the mapping technique of FIG. 8, which employs a pacing probe that may also be used to identify pacing sites having acceptable capture thresholds. In one example, at step 604, the pacing probe is controlled to deliver pacing pulses at a candidate site and capture is verified. If capture cannot be verified, then the site is excluded. If capture is verified, then the activation time for that site is measured for use in determining the optimal pacing location. Another technique for determining whether to exclude sites based on capture threshold is to examine the morphology of the evoked response (ER)—assuming a response is evoked. The pertinent parameters of the ER morphology include pacing latency (i.e. the time delay from the pacing pulse to a minimum ER or to the onset of ER or to the maximum slope (DMAX)), the area integral below the rest potential or paced depolarization integral (PDI) and the value of DMAX). Assuming a constant pacing pulse amplitude, a site is excluded if the value of the morphological parameter is below or above a predetermined threshold, which may be set based on routine experimentation. The ER-based technique can thus be used to identify infarcted or ischemic sites.

However, the capture-based technique may also be employed in connection with the other mapping techniques described herein. For example, mapping techniques may be performed by first using a sensing probe to identify one optimal location within each region of the heart chamber being tested—based solely on activation times. Thereafter, a pacing probe is placed at each of the identified locations to determine whether its capture threshold is acceptable, then the physician selects a particular location having an acceptable capture threshold for actually implanting a pacing electrode. As can be appreciated, the capture thresholds-based techniques of FIG. 9 may be exploited in a wide variety of specific implementations consistent with principles of the invention.

Exemplary ECG-Based Methods

As already mentioned surface ECG information can be helpful in assessing cardiac condition. In particular, such information can be used in determining whether a patient is likely to respond to CRT. Further, as described herein, ECG information can help in determining one or more stimulations sites for CRT and, more particularly, one or more stimulation sites for stimulation of the left ventricle.

Figure 10:
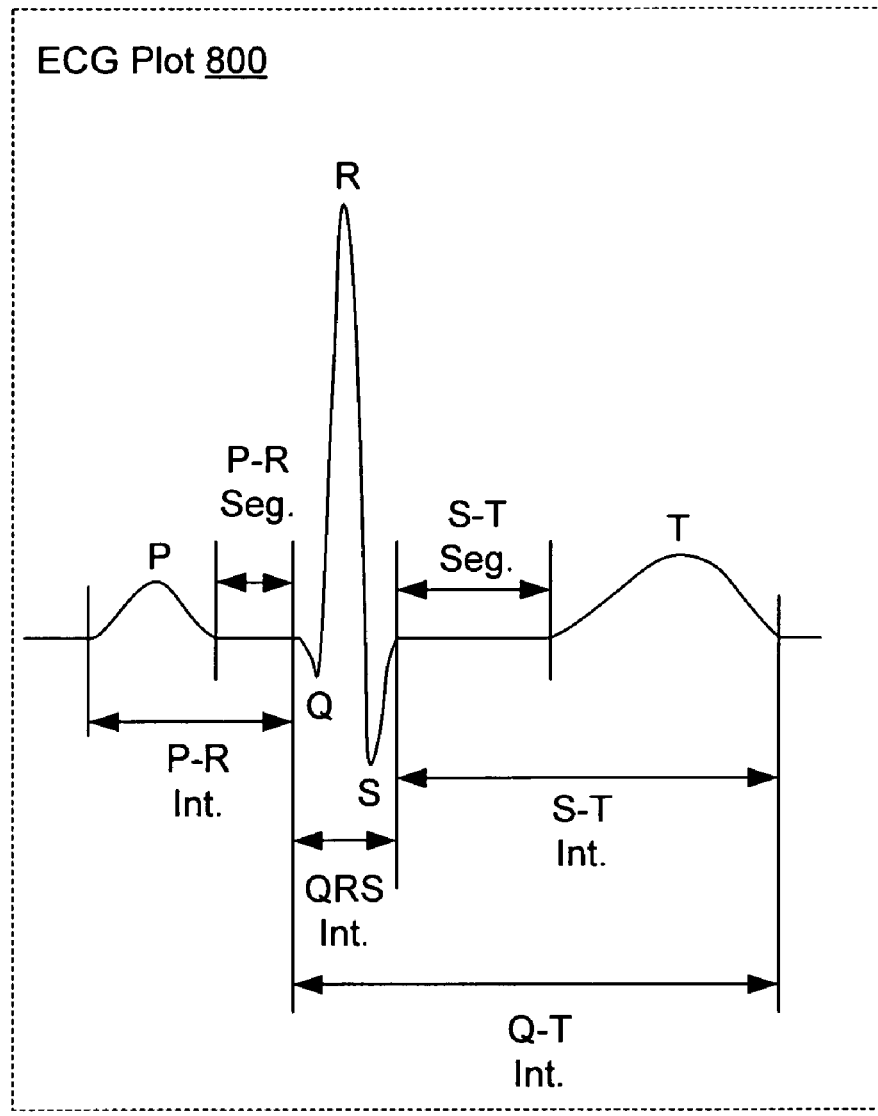
FIG. 10 is a stylized plot of a surface ECG.

FIG. 10 shows a plot 800 of a stylized surface ECG for one cardiac cycle. The plot 800 includes various peaks, segments and intervals, some of which have been mentioned above. While one plot is shown in FIG. 10, depending on specific features of the ECG acquisition system used, multiple plots may be acquired. For example, a multiple lead ECG acquisition system can acquire multiple plots for a single cardiac cycle. In general, each plot is associated with a different lead configuration and hence shapes and timings of the various peaks, segments and intervals may vary from plot to plot.

Most ECG acquisition systems rely on multiple leads. For example, one fairly standard multiple lead ECG acquisition system relies on 7 leads while another relies on 12 leads. The standard 7 lead system includes leads labeled I, II, III, aVR, aVL and aVF while the standard 12 lead system also includes leads labeled V1 through V6. The labels correspond to surface positions with respect to the body.

Given this brief background on multiple lead ECG acquisition systems, the various components of the ECG plot 800 are now described. The peak labeled "P" corresponds to a P wave caused by depolarization of the atrial myocardium. A normal P wave usually has a width of less than about 110 ms. Depending on lead configuration, a P wave is usually positive and rounded in leads I, II, and aVF in about 94% of normal individuals and usually negative in aVR. The P wave axis is about 60°.

An interval that is measured from the beginning of a P wave to the beginning of the QRS complex, is referred to as the PR interval, which represents atrial depolarization plus an AV nodal delay. The PR interval is typically in a range from about 120 ms to about 200 ms. Where AV conduction is impaired, the PR interval is lengthened (e.g., first-degree AV block). The PR interval includes the PR segment, which begins at the end of the P wave and ends with the onset of the QRS complex. Elevation of the PR segment may indicate disease such as atrial infarction or pericarditis. Depression of the PR segment may occur if a large atrial repolarization wave exists.

While labeled as individual peaks in the plot 800, the QRS complex represents depolarization of the ventricular myocardium. While depolarization of the AV node, His bundle, bundle branches, and Purkinje fibers also occurs, the electrical signals emerging from these cardiac structures are typically too small in amplitude to be detected by electrodes on the body surface.

According to some conventions, positive waves of the QRS complex are labeled R waves. Further, if more than one positive peak exists, then the second positive peak is labeled R'. In some conventions, an upper case capital letter "R" is used to describe a sizable R wave and a lower case letter "r" is used to describe a small R wave. Negative waves of the QRS are typically labeled with "Q", referred to as Q waves, which precede the R wave or labeled with "S", referred to as S waves, which follow the R wave. Again, relative size may be denoted by use of upper or lower case letters. Although termed the "QRS" complex, many complexes do not contain all three waves distinctly.

A "normal" QRS complex will typically have a width ranging from about 70 ms to about 110 ms. Some conventions for 12-lead ECG measurements consider the widest QRS measurement as the most correct. Many consider leads I and V1 as providing the most accurate QRS complex width.

In a multi-lead measurement system, a progression typically occurs for the R wave. In the precordial leads, the QRS complex starts off primarily negative (rS) in V1 and gradually becomes primarily positive (qRs) with the tallest R wave in V5 or V6. The transition from mostly negative to mostly positive typically occurs between V3 and V4. Normally the R wave in V6 is always less in magnitude than the R wave in V5. Precordial R waves are usually sensitive to lead placement; a factor that should be considered for interpretation of R wave progression.

Various conditions may be determined on the basis of the R wave or R wave progression. For example, an early R wave in leads V1 and V2 having a magnitude as large as those in the next several leads (e.g., V3, V4, V5) can reflect posterior infarction, lateral MI, right ventricular hypertrophy (RVH), or septal hypertrophy. Also consider a large magnitude R wave in V1, which may indicate RVH, posterior MI, or Wolff-Parkinson-White (W-P-W).

Small magnitude R waves in the right precordial leads may be due to left ventricular hypertrophy (LVH), left anterior fascicular block (LAFB), COPD, or MI. LVH causes loss of R wave magnitude from V1-V3 without MI. Loss of R magnitude between V1-V2 or V2-V3 in the absence of LVH suggests anterior MI.

A poor R wave Progression, e.g., R waves that do not begin to dominate the QRS complex until V5 or V6, may represent infarction or injury of the anterior LV.

With respect to the Q Wave, not all leads may record a Q wave. Normal Q waves typically represent septal depolarization. Q waves should be distinguished from pathologic Q waves that can indicate myocardial infarction.

A "normal" Q wave is usually present in leads I, aVL, V5, and V6 (left lateral leads) only and has a width of about 4 ms. A small Q wave may be evidenced in aVF and V5 leads. Lack of a Q wave may indicate septal fibrosis; whereas, a large Q wave (magnitude), may indicate myocardial damage, as large, diagnostic Q waves represent altered electrical activity in the myocardium due to transmural myocardial damage. Note however that a diagnostic Q wave in V1, aVL, or III may be present without indicating myocardial damage.

An ST segment commences at the "J point" (end of the QRS complex) and ends at the onset of the T wave. The ST segment represents the duration for which ventricular cells are in the plateau phase (phase 2) of the action potential (where there is no current flow and thus little, if any transmembrane gradient). QRS complex width and ST segment also represent the duration of the ventricular absolute refractory period, where the ventricles will generally not respond to stimulation. The ST segment should be isoelectric with a smooth contour. In instances where it is not isoelectric, the ST segment may be characterized as ST depression or ST elevation.

The QT Interval is a measure of the refractory period during which the myocardium would not respond to a second impulse and it is typically measured from the beginning of the QRS complex to the end of the T wave. Some consider leads V2 or V3 as providing the most accurate QT interval. A basic rule indicates that the QT interval should be roughly less than half the preceding RR interval. QT interval normally varies with heart rate. QT interval may also be affected by width of the QRS complex such as a bundle branch block, which increases the QT interval. Thus, ST interval may be considered to compensate for a wide QRS complex.

A measure referred to as QT dispersion is determined on the basis of QT intervals from various (or all) ECG leads where the shortest QT interval ($QT_{Min}$) is subtracted from the longest QT interval ($QT_{Max}$). A substantial difference between these two QT intervals may indicate that heterogeneous refractoriness exists and that the patient may be at higher risk of cardiac death from development of ventricular tachycardia/fibrillation, especially from any proarrhythmic effects of antiarrhythmic drugs.

JT intervals may be measured to reflect repolarization. The JT interval is sometimes used to measure the refractory period in patients treated with a Na+ channel blocker antiarrhythmic drugs (e.g., Quinidine, Pronestyl, and other class I agents), which slow depolarization and prolong the QRS complex.

The T wave represents repolarization of the ventricles and the earliest the ventricles can respond to another stimulus usually coincides with the apex of the T wave. The T wave should have the same polarity as the QRS complex, i.e., if the QRS complex is primarily negative, the T wave should be negative.

ST deviation and T wave abnormalities are seen with conditions other than myocardial ischemia such as a wide QRS complex or secondary to effects of medications. It is possible to have both primary and secondary changes (e.g., bundle branch block plus ischemia). In this case, the ST segment may appear to normalize because both ST depression and elevation are occurring simultaneously.

Where various ECG signals are available (e.g., from a multi-lead ECG system), R peaks, PR intervals, PR segments, QRS intervals, QR intervals, RS intervals, ST intervals, QT intervals, etc., may be used to assign a probability of responding to CRT or make another type of assessment with respect to CRT. Dispersions, subtractions, additions, ratios, maxima, minima, etc., of the aforementioned measures may be used. With respect to subtractions, where the value of RS interval minus QR interval is greater than a certain value (e.g., a threshold), then this may indicate a greater likelihood of responding to CRT. Thus, an exemplary method optionally relies, at least in part, on a difference between QR interval and RS interval. Of course, use of QRS interval may substitute for QR interval or RS interval (e.g., QR interval=QRS interval−RS interval).

With respect to maxima, an exemplary method optionally determines a maximum RS interval from multi-lead ECG information and then assigns a probability of responding to CRT and/or selects one or more CRT settings based at least in part on the maximum RS interval. For example, the maximum RS interval may be compared to predetermined ranges or values or may be compared to historical values to assign a probability or to make a selection of a CRT setting.

As mentioned in the Background, in some instances, a subject may have a narrow QRS yet still benefit from CRT. As described herein, determinations and analyses of measures such as RS interval alone or with reference to one or more other measures, may help identify such subjects and optionally help in selecting one or more CRT settings.

While various measures have been mentioned with respect to one or more surface ECGs (e.g., depending on number of leads, etc.), other measures may be used, alternatively, or in addition to the aforementioned measures. For example, the time of a peak in a wave (e.g., R wave peak time), the time for a maximum in dV/dt, time, the time of commencement of a wave (e.g., R wave commencement time), the time of an end of a wave (e.g., R wave end time), differences between various times (e.g., difference between peak of an R wave and end of an R wave).

Figure 11:
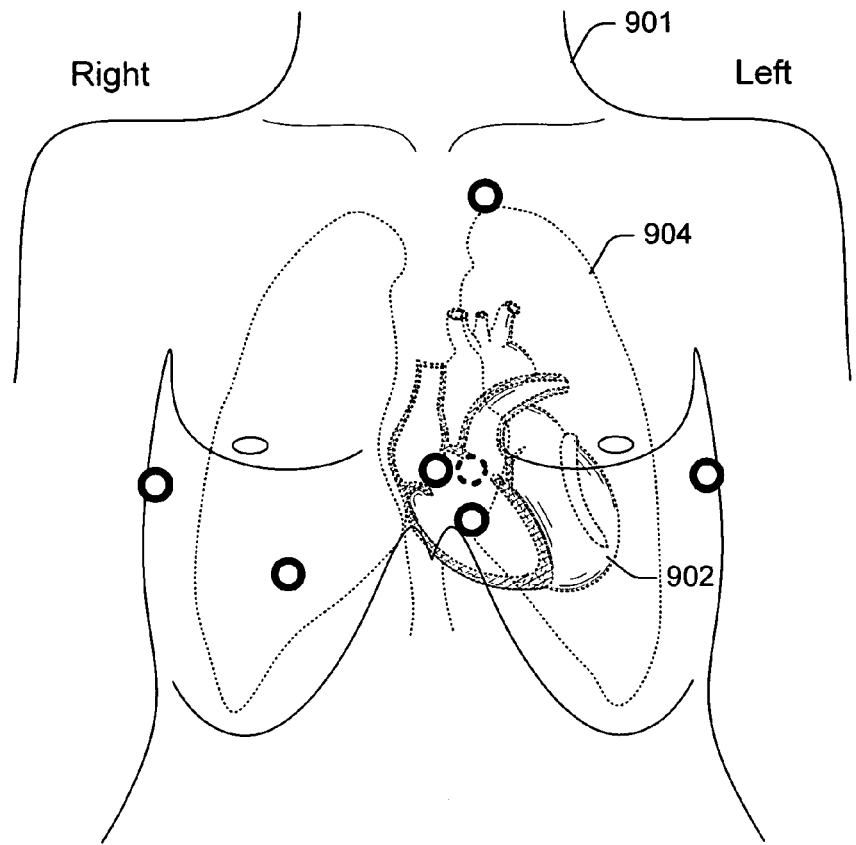
FIG. 11 is a schematic of an exemplary seven lead surface ECG arrangement with reference to the heart, the lungs and the torso.
Figure 11:
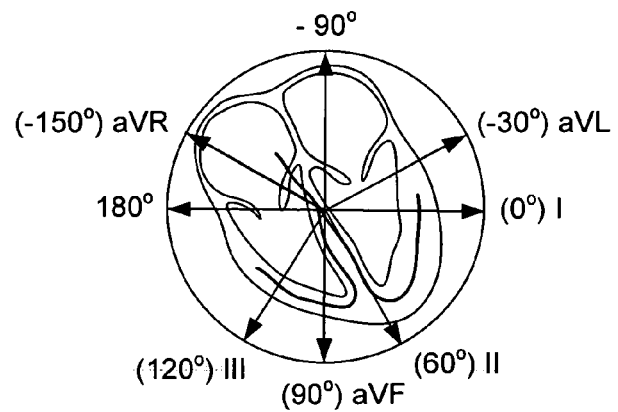

Various leads were mentioned with respect to the ECG plot 800 of FIG. 10. FIG. 11 shows a body 900 with placement positions for 7 leads and a volumetric coordinate system 940 associated with the positions and the heart. Each lead perceives the heart electrically from a particular point of view. Leads II, III and aVF perceive the inferior surface while leads I and aVL perceive the left lateral wall. Again, most graphical representations of an ECG use a lead I representation.

The body 900 further indicates approximate positions for the heart 902 and the lungs 904. The lead positions are indicated by circles, where one circle has a dashed line as it is positioned on the backside of the body 900.

The coordinate system 940 indicates approximate positions for the four chambers of the heart and a central conduction path with right and left ventricular branches. The acronym aVL refers to "augmented voltage left", the acronym aVR refers to "augmented voltage right" and the acronym aVF refers to "augmented voltage foot".

Figure 12:
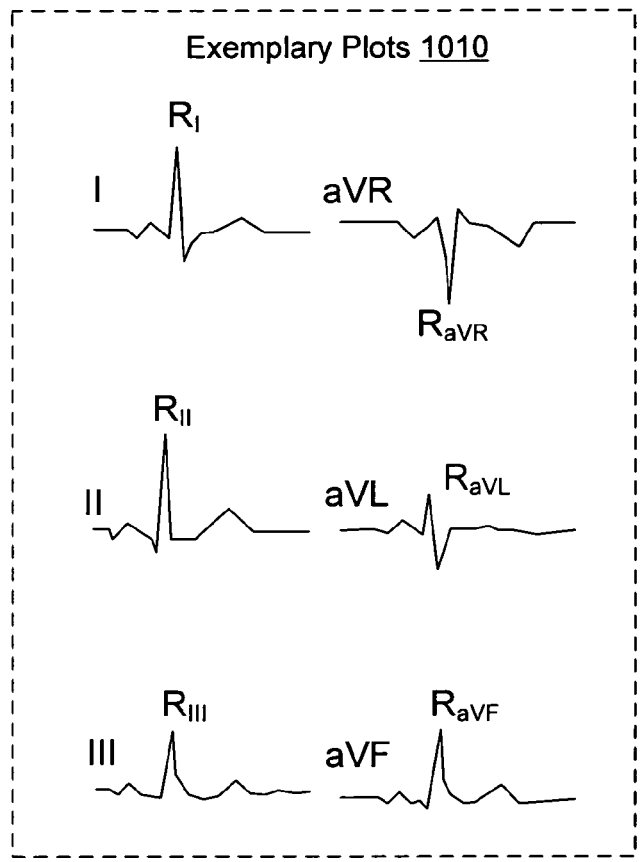
FIG. 12 is a series of ECG plots and exemplary measures suitable for helping determine one or more stimulation sites.

The foregoing discussion with respect to FIG. 10 may be referenced to the various ECG plots 1010 of FIG. 12 (see also coordinate system of FIG. 11). FIG. 12 also includes various exemplary measures 1020. The ECG plots 1010 include peak R wave labels $R_I$, $R_{II}$, $R_{III}$, $R_{aVR}$, $R_{aVL}$ and $R_{aVF}$ and the measures 1020 indicate various exemplary minima and maxima. The time of each peak may be determined using any of a variety of techniques. Once determined, a minimum time may be determined and a maximum time determined for a peak R wave. The difference between these two times is referred to herein as ΔR. ΔR represents dispersion in the peak of the R wave as measured by the various leads.

As mentioned in the background section, ECG information is electrical information. This information inherently reflects mechanical information of the heart. Exemplary measures such as ΔR uncover cardiac mechanics. In particular, exemplary measures such as ΔR may uncover ventricular mechanics (e.g., synchrony, dyssynchrony).

Figure 13:
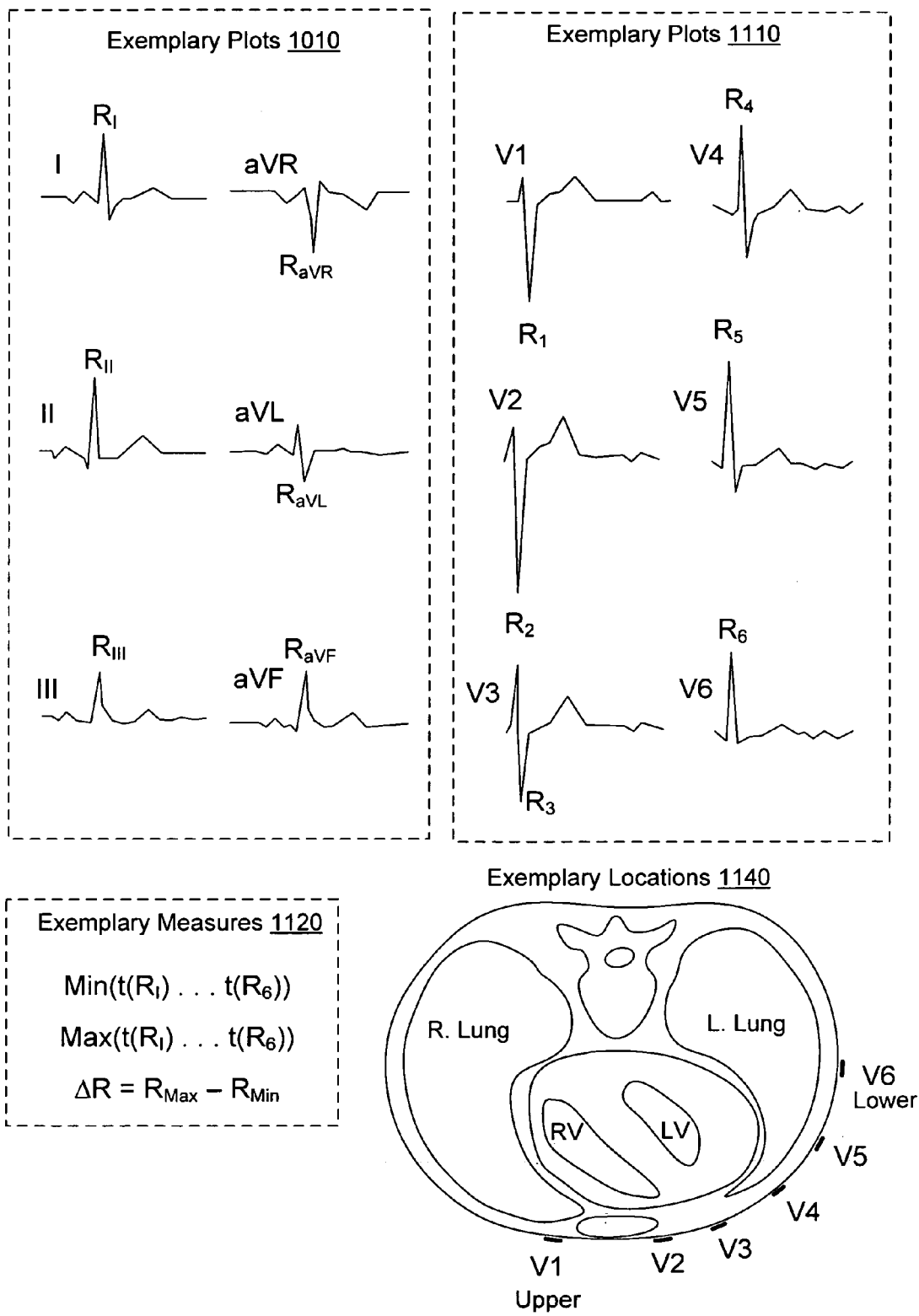
FIG. 13 is a series of ECG plots, exemplary measures and a schematic of conventional lead locations with reference to the heart, the lungs and the torso.

The foregoing discussion with respect to FIG. 10 may be referenced to the various plots 1110 of FIG. 13, which includes the plots 1010 of FIG. 12 for convenience. Also shown in FIG. 13 are various exemplary measures 1120 and a diagram of exemplary locations 1140 that indicate approximate placement positions for the precordial leads V1-V6, noting that they may be in approximately the same plane or not. As already mentioned, peak times may be measures. The plots 1110 include peak R wave labels: $R_1, R_2, R_3, R_4, R_5$ and $R_6$. The time of each peak may be determined using any of a variety of techniques. Once determined, a minimum time may be determined and a maximum time determined for the peak R waves. The difference between these two times is referred to herein as $\Delta R$. $\Delta R$ represents dispersion in the peak of the R wave as measured by the various leads.

An exemplary method may determine a maximum peak time and a minimum peak time from multi-lead ECG information and use these times to determine peak dispersion. Such peak dispersion may be used to indicate ventricular mechanics (e.g., synchrony or dyssynchrony).

While the foregoing discussion of ECG information pertains mainly to ventricular mechanics, such information may aid in determining one or more stimulation sites for stimulation of the right ventricle and/or the left ventricle. Further, such ECG information may be combined with aforementioned techniques for modeling the body, in particular, modeling of the heart with respect to other body parts, fluid, etc.

An example of site selection follows whereby ECG information is used to characterize cardiac tissue. More specifically, the example pertains to ECG information indicative of myocardial infarction or ischemia and characterization of such cardiac conditions.

A review by Wellens and Gorgels ("The Electrocardiogram 102 Years After Einthoven", Circulation 2004 109: 562-564) discusses various efforts to relate ECG measures to cardiac condition. For example, a ST segment deviation score can help estimate the size of an area at risk of myocardial infarction. The ST segment deviation score is determined by counting the number of millimeters (on a chart) that the ST segment deviates (elevated or depressed) from the isoelectric line in a 12-lead ECG where the higher the ST-segment deviation number, the larger the area at risk. While such a technique may help in selecting a stimulation site, various more sophisticated techniques (e.g., computerized or otherwise automated) can more readily and/or accurately characterize cardiac condition for purposes of selecting one or more stimulation sites.

Figure 14:
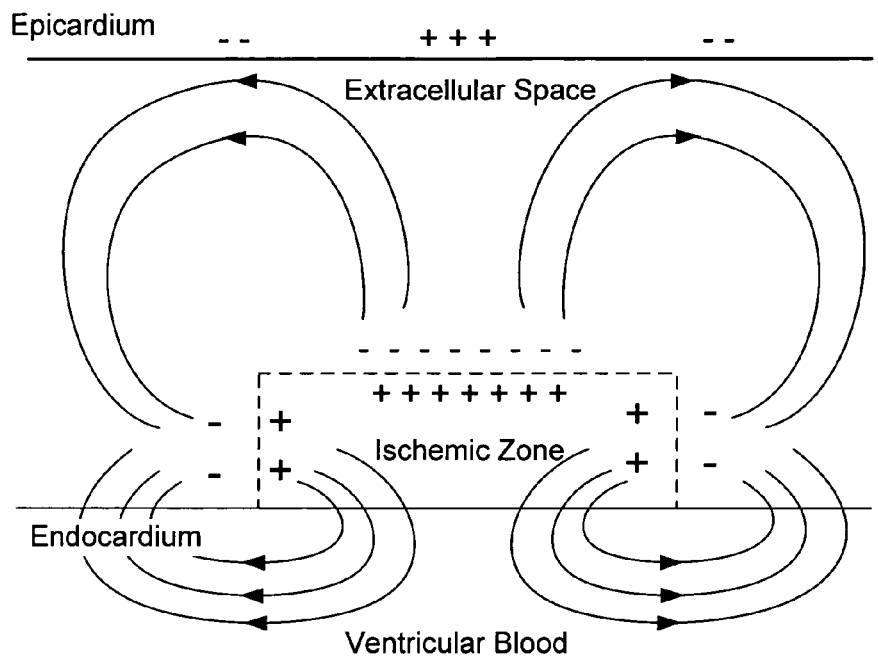
FIG. 14 is a schematic and an associated electrical circuit of an exemplary scenario of conduction in the heart where an ischemic zone exist in the myocardium.
Figure 14:
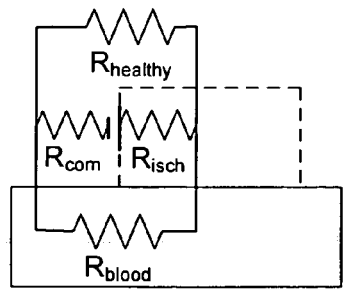

One particular technique involves relating the heart to an electrical model. FIG. 14 shows a scenario of cardiac ischemia 1200 that includes a schematic of a myocardial region 1210 and an approximate electrical circuit representation 1220 of the myocardial region 1210. This scenario is discussed in further detail in a study by Hopenfeld et al., "The Effect of Conductivity on ST-Segment Epicardial Potentials Arising from Subendocardial Ischemia", *Annals of Biomed. Eng.*, 33(6): 751-763, 2005.

The schematic 1210 shows a myocardial region bounded by the epicardium and the endocardium, which is adjacent ventricular blood. An ischemic zone exists in the myocardial region adjacent the endocardium. The electrical circuit 1220 shows four resistances. The resistance $R_{healthy}$ corresponds to healthy myocardium, the resistance $R_{isch}$ corresponds to ischemic myocardium, the resistance $R_{blood}$ corresponds to blood and the resistance $R_{comm}$ corresponds to healthy myocardium common to current loops traveling through ventricular blood and from the epicardial side of the ischemic patch.

Through use of such a model, Hopenfeld et al. concluded that ST segment depression occurs over a lateral boundary between healthy and ischemic tissue for the case of medium or thick ischemia. Further, Hopenfeld et al. noted that when an area of injury is confined to the subendocardium, the ST segment deviates downward causing ST depression in the leads facing the area of injury. They also noted that in the setting of myocardial infarction, injury is more likely to be transmural (i.e., involving the full thickness of the ventricle) and that, in this case, the ST segment deviates upward causing ST elevation in the leads facing the area of injury.

As described herein, an exemplary method can acquire surface ECG information, analyze the information for the presence of ST segment deviation (e.g., elevation or depression) and then use the analysis for selecting one or more stimulation sites. For example, where a medium or thick ischemic region exists, placement of a stimulation electrode at that site may be avoided. Further, placement of a stimulation electrode near the ischemic region may occur where characteristics of such tissue are taken into account for delivery of stimulation. For example, borderline regions (bordering an ischemic region) are known to have some delay in initiation of contraction where different border regions may have different delays (e.g., dispersion). Hence, delays for border regions may be determined for purposes of delivery of stimulation locally or remote from the border region(s). A particular example acquires electrical information from one or more border regions and establishes a relationship to myocardial mechanics. In turn, a therapy is selected or optimized based on the myocardial mechanics in a manner that accounts for the ischemic region and border thereof.

In the foregoing surface ECG example, the analysis of the surface ECG information optionally relies on a plurality of ST segments for one or more cardiac cycles to characterize the cardiac condition. Such characterization typically aims to identify and localization one or more ischemic regions to aid in selecting one or more ventricular stimulation sites.

Various exemplary methods optionally use multi-lead ECG information in conjunction with an inverse solution technique to localize healthy and/or unhealthy myocardium for purposes of selecting one or more ventricular stimulation sites. An inverse solution technique involves acquiring ECG information and optionally other information and then determining characteristics responsible for generation of the ECG information.

Figure 15:
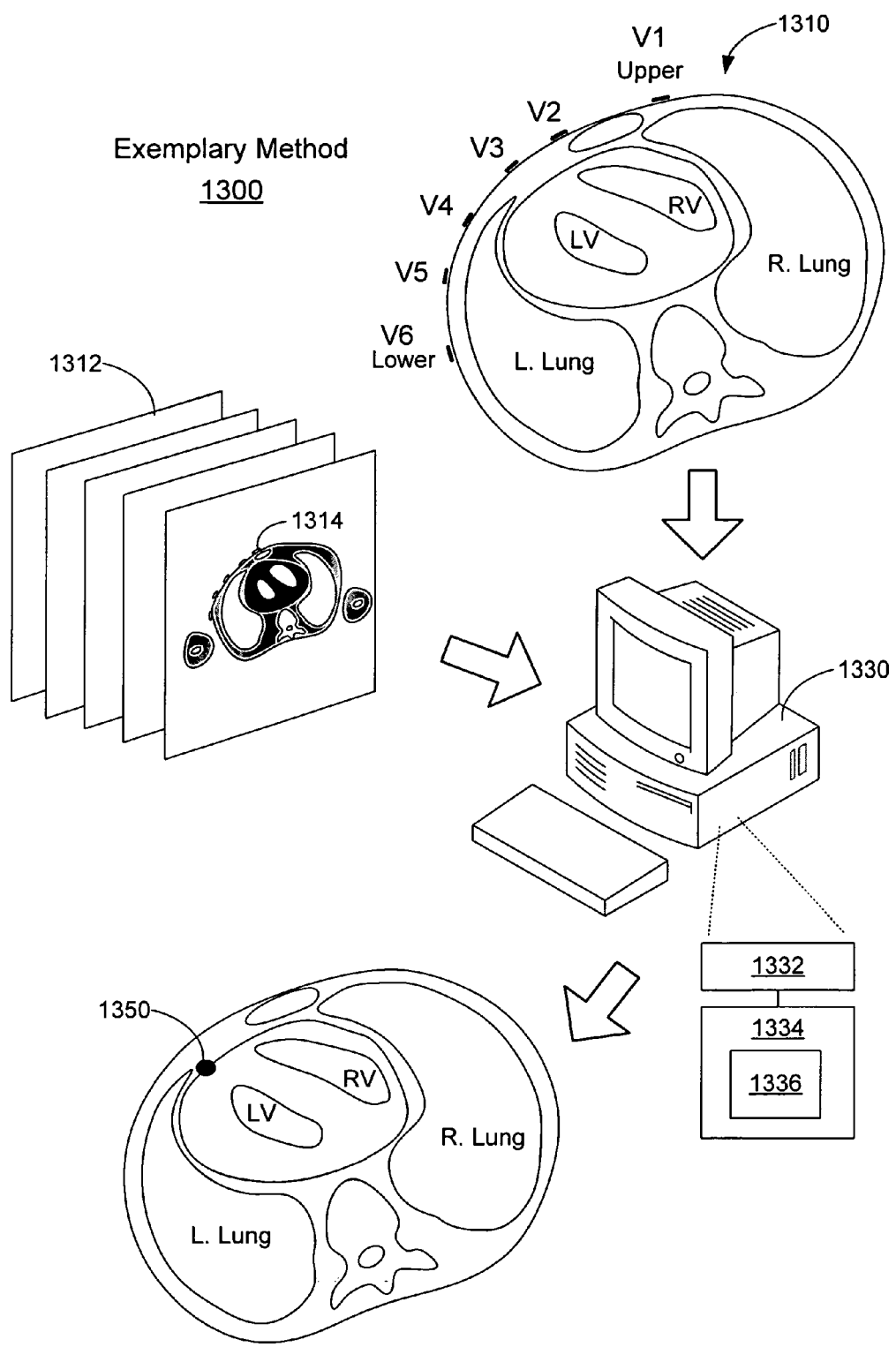
FIG. 15 is a diagram of an exemplary method that includes representations of data and a computing device with a processor, memory and instructions.

FIG. 15 shows an exemplary method 1300 for selecting or determining a stimulation site. The method 1300 includes various processes including providing ECG information 1310, providing other information 1312 and selecting or determining a stimulation site 1350.

In the example of FIG. 15, ECG information 1310 for a patient is available as well as other information 1312. The ECG information is acquired using a multi-lead ECG system. The other information 1312 is acquired using an imaging technique such as magnetic resonance imaging (MR) or computerized tomography X-ray imaging (CT). Other imagining techniques such as ultrasound imaging, emission tomography, etc., may be used. Further, spectroscopic techniques may be employed (e.g., magnetic resonance spectroscopy) to provide information other than ECG information; however, depending on circumstances (e.g., cardiac condition), ECG information alone may suffice without having to acquire other information (e.g., MR, CT, tissue Doppler, echocardiograph, etc.).

The information 1312 can be a 3-D data set that optionally includes positions of fiducials 1314. In general, a fiducial is a marker, visible using the imaging modality, that references a position of interest. For example, the fiducials 1314 correspond to the locations of ECG leads as positioned for acquisition of the ECG information 1310. Thus, use of fiducials acts to cross-link the ECG information 1310 with the other information 1312. Or, in other words, the other information 1312 includes information germane to the ECG information 1310 such as positions of various ECG leads on the body of a patient.

In general, the exemplary method 1300 relies on a computer 1330. The computer 1330 includes a processor 1332, one or more computer-readable media 1334 (e.g., memory, etc.) and instructions 1336 (e.g., software or firmware). The instructions 1336 cause the processor 1332 to perform logic operations associated with the method 1300. The computer 1330 may receive information in any of a variety of manners such as via a wired or wireless network interface, via a transportable medium, etc.

As already mentioned, the method 1300 aims to identify one or more stimulation sites 1350. While CRT generally includes stimulation of one or both ventricles at one or more ventricular stimulation sites, such the method 1300 may identify sites for other purposes, for example, atrial stimulation.

Figure 16:
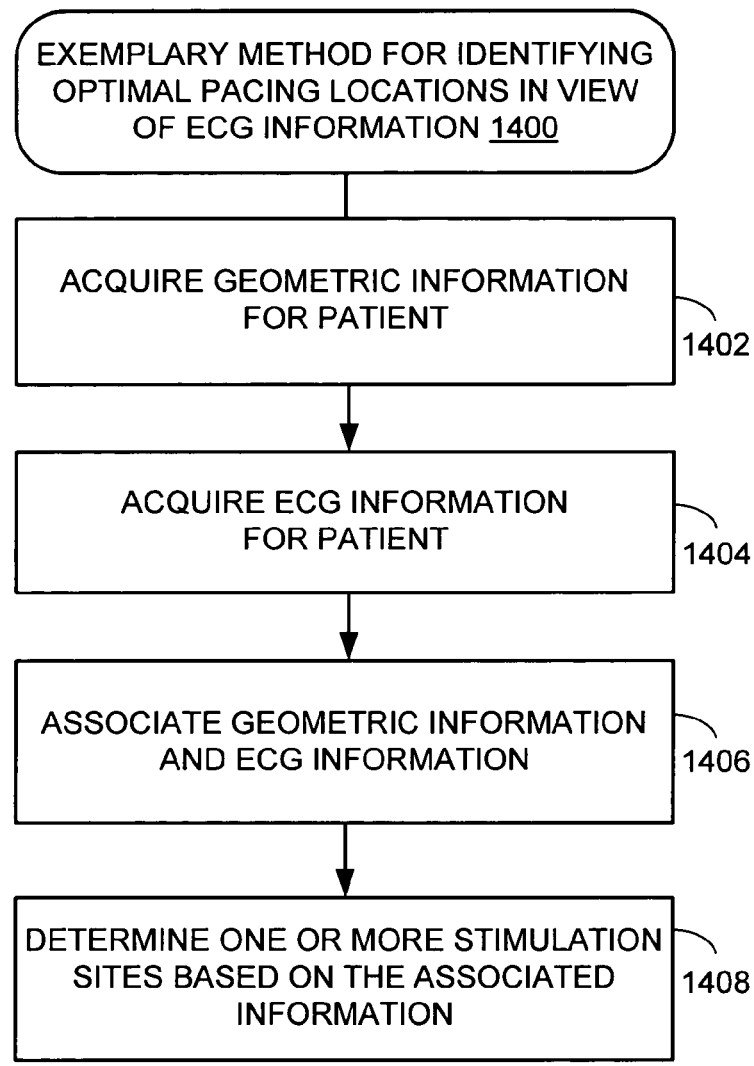
FIG. 16 is a block diagram of an exemplary method for determining one or more stimulation sites based on geometric information and ECG information.

FIG. 16 shows an exemplary method 1400 for identifying optimal pacing locations in view of ECG information. The method 1400 includes acquiring geometric information for a patient 1402. Geometric information may be acquired through machine or human measurements. Such geometric information typically includes dimensions for a patient's torso. More particularly, such geometric information is germane to the propagation of electrical signals in a patient's body. For example, a multi-lead ECG system detects electrical cardiac activity using electrodes positioned on the surface of a patient's body. The geometric information can help to identify distances between an electrode and the heart and optionally the type or types of tissue that lie between the electrode and the heart. The aforementioned imaging modalities are suitable for acquiring geometric information.

Another type of geometric information pertains to blood vessels and their geometric relationship to the heart. For example, geometric information can include positions of epicardial veins suitable for placement of one or more stimulation electrode. Geometric information can include position and size of venous structures such as the coronary sinus and contributories thereto.

The method 1400 also includes acquiring ECG information. In general, a multi-lead ECG system is used to acquire such information. After or during acquisition of the ECG information and the geometric information, the method 1400 associates the ECG information and geometric information 1406. In general, the association aims to understand better the ECG information as it relates to cardiac condition. The process of associating may occur through input of ECG lead positions with reference to a geometric model based on the geometric information and input of ECG information acquired using the ECG lead positions.

The method 1400 then determines one or more stimulation site based at least in part on the associated information 1408. The determination may be made using possible venous sites or other structures as limiting factors. For example, a determination may indicate "optimal" placement in a location that would also cause undesirable activation of a nerve. However, if the possible sites are limited according to various criteria, then a site given as a solution to the site problem is likely to be a practical site.

As an example, consider the ECG information 1310 and the imaging information 1312 as bases for selection the stimulation site 1350 of FIG. 15. In this example, the imaging information 1312 optionally includes locations of epicardial veins suitable for receiving an electrode bearing lead. Thus, site selection is a function of ECG information acquired using a multi-lead ECG system and 3-D imaging information of the heart (e.g., epicardial veins, etc.). Further, through the use of fiducials to mark lead locations, accuracy is increased in relating the ECG information to the imaging information.

Of course, the imaging information may include spectroscopic information that indicates cardiac condition such as, but not limited to, wall thickness, ischemia, position of myocardium with respect to time, etc. Other information may include IEGM information, from an implantable device with one or more electrodes (e.g., an existing pacing system, etc.).

Overview of Exemplary External Programmer

FIG. 17 illustrates pertinent components of an external programmer 1600 for use in programming an implantable medical device 10 such as a pacemaker or ICD. The external programmer 1600 optionally receives information from other diagnostic equipment 1550, which may be an imaging unit such as a MR unit, CT unit, ultrasound unit, etc. Briefly, the programmer 1600 permits a physician or other user to program the operation of the implanted device 10 and to retrieve and display information received from the implanted device 10 such as IEGM data and device diagnostic data. Additionally, the external programmer 1600 receives and displays ECG data from separate external ECG leads 1632 that may be attached to the patient. The programmer 1600 optionally receives ECG information from an ECG unit external to the programmer 1600.

Depending upon the specific programming of the external programmer 1600 may also be capable of processing and analyzing data received from the implanted device 10 and from ECG leads 1632 to, for example, render diagnosis as to medical conditions of the patient or to the operations of the implanted device 10. As noted, the programmer 1600 is also configured to receive data representative of conduction time delays from the atria to the ventricles and to determine, therefrom, an optimal or preferred location for pacing. Further, the programmer 1600 may receive information such as ECG information, IEGM information, information from diagnostic equipment, etc., and determine one or more stimulation sites (e.g., consider the method 1300 and the method 1400). With respect to the method 1300, the programmer 1600 optionally substitutes for the computer 1330 and ECG information 1310 is optionally acquired by the programmer 1600 or by another ECG unit.

Now, considering the components of programmer 1600, operations of the programmer are controlled by a CPU 1602, which may be a generally programmable microprocessor or microcontroller or may be a dedicated processing device such as an application specific integrated circuit (ASIC) or the like. Software instructions to be performed by the CPU are accessed via an internal bus 1604 from a read only memory (ROM) 1606 and random access memory 1630. Additional software may be accessed from a hard drive 1608, floppy drive 1610, and CD ROM drive 1612, or other suitable permanent or removable mass storage device. Depending upon the specific implementation, a basic input output system (BIOS) is retrieved from the ROM 1606 by CPU 1602 at power up. Based upon instructions provided in the BIOS, the CPU 1602 "boots up" the overall system in accordance with well-established computer processing techniques.

Once operating, the CPU 1602 displays a menu of programming options to the user via an LCD display 1514 or other suitable computer display device. To this end, the CPU 1604 may, for example, display a menu of specific programming parameters of the implanted device 10 to be programmed or may display a menu of types of diagnostic data to be retrieved and displayed. In response thereto, the physician enters various commands via either a touch screen 1516 overlaid on the LCD display or through a standard keyboard 1518 supplemented by additional custom keys 1520, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

With regard to the determination of the optimal pacing location, CPU 1602 includes an optimal pacing location identification system 1646 and a 3-D mapping system 1647. The location identification system can optionally input data representative of time delays from the right atrium to the candidate locations in the ventricles, either from a sensing probe, the implanted device, or an EKG. The location identification system 1646 optionally includes control logic to associate information and to determine one or more stimulation sites. The location identification system may also include control logic to analyze information to aid in such a determination.

Where information is received from the implanted device 10, telemetry wand 1628 may be used. Other forms of wireless communication exist as well as forms of communication where the body is used as a "wire" to communicate information from the implantable device 10 to the programmer 1600.

If information is received directly from a mapping probe, any appropriate input may be used, such as parallel IO circuit 1640 or serial IO circuit 1642. Mapping information received via a mapping probe or via other diagnostic equipment (e.g., the imagining unit 1550) may be analyzed using the mapping system 1647. In particular, the mapping system 1647 (e.g., control logic) may identify fiducial markers in imaging data received from an imaging unit and relate the positions of the fiducial markers to, for example, ECG lead positions. Alternatively, although not shown, a separate dedicated input port for receiving signals from a mapping probe may be provided. A communication interface 1645 optionally allows for wired or wireless communication with diagnostic equipment 1550 or other equipment. The communication interface 1645 may be a network interface connected to a network (e.g., intranet, Internet, etc.). In any case, as already explained, the external programmer determines the optimal location based at least in part on ECG information and other information such as geometric information (e.g., MR, CT, ultrasound, etc.). The mapping system 1647 provides display information for the optimal location and/or various candidate locations on a map or model of the heart. The mapping system 1647 optionally provides information as to relative propagation time delay values detected at one or more locations (e.g., stimulation sites).

The map or model is displayed using display 1514 based, in part, on 3-D heart information and optionally 3-D torso information that facilitates interpretation of surface ECG information. Such 3-D information may be input via ports 1640, 1642, 1645 from, for example, a database, a 3-D imaging system, a 3-D location digitizing apparatus (e.g., sterotactic localization system with sensors and/or probes) capable of digitizing the 3-D location. According to such an example, a physician can thereby view the optimal location on the map of the heart to ensure that the location is acceptable before an electrode or electrodes are positioned and optionally fixed at that location. The programmer 1600 optionally records procedures and allows for playback (e.g., for subsequent review). For example, the heart map and all of the time delay data may be recorded for subsequent review, perhaps if an electrode needs to be repositioned. Electrodes may be lead based or non-lead based, for example, an implantable device may operate as an electrode and be self powered and controlled or be in a slave-master relationship with another implantable device (e.g., consider a satellite pacemaker, etc.).

Once all pacing leads are mounted and all pacing devices are implanted (e.g., master pacemaker, satellite pacemaker, biventricular pacemaker), the various devices are optionally further programmed.

In a typical process, a physician initially controls the programmer 1600 to retrieve data stored within an implanted device(s) and to also retrieve ECG data from ECG leads, if any, coupled to the patient. To this end, CPU 1602 transmits appropriate signals to a telemetry subsystem 1622, which, in this example, provides components for directly interfacing with the implanted device(s), and the ECG leads.

The telemetry subsystem 1622 may include its own separate CPU 1624 for coordinating the operations of the telemetry subsystem. In a dual CPU system, the main CPU 1602 of programmer communicates with telemetry subsystem CPU 1624 via internal bus 1604. Telemetry subsystem additionally includes a telemetry circuit 1626 connected to telemetry wand 1628, which, in turn, receives and transmits signals electromagnetically from a telemetry unit of the implanted device. The telemetry wand is placed over the chest of the patient near the implanted device to permit reliable transmission of data between the telemetry wand and the implanted device.

Typically, at the beginning of the programming session, the external programming device controls the implanted device(s) via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like.

Data retrieved from the implanted device(s) can be stored by external programmer 1600 (e.g., within a random access memory (RAM) 1630, hard drive 1608, within a floppy diskette placed within floppy drive 1610). Additionally, or in the alternative, data may be permanently or semi-permanently stored within a compact disk (CD) or other digital media disk, if the overall system is configured with a drive for recording data onto digital media disks, such as a write once read many (WORM) drive. Where the programmer 1600 has a communication link to an external storage device or network storage device, then information may be stored in such a manner (e.g., on-site database, off-site database, etc.). The programmer 1600 optionally receives data from such storage devices.

A typically procedure includes transferring all patient and device diagnostic data stored in an implanted device to the programmer 1600. The implanted device(s) may be further controlled to transmit additional data in real time as it is detected by the implanted device(s), such as additional IEGM data, lead impedance data, and the like. Additionally, or in the alternative, telemetry subsystem 1622 receives ECG signals from ECG leads 1632 via an ECG processing circuit 1634. As with data retrieved from the implanted device itself, signals received from the ECG leads are stored within one or more of the storage devices of the programmer 1600. Typically, ECG leads output analog electrical signals representative of the ECG. Accordingly, ECG circuit 1634 includes analog to digital conversion circuitry for converting the signals to digital data appropriate for further processing within programmer 1634. Depending upon the implementation, the ECG circuit 1643 may be configured to convert the analog signals into event record data for ease of processing along with the event record data retrieved from the implanted device. Typically, signals received from the ECG leads 1632 are received and processed in real time.

Thus, the programmer 1600 is configured to receive data from a variety of sources such as, but not limited to, the implanted device 10, the diagnostic equipment 1550 and directly or indirectly via external ECG leads (e.g., subsystem 1622 or external ECG system). The diagnostic equipment 1550 includes wired 1554 and/or wireless capabilities 1552 which optionally operate via a network that includes the programmer 1600 and the diagnostic equipment 1550 or data storage associated with the diagnostic equipment 1550.

Data retrieved from the implanted device(s) typically includes parameters representative of the current programming state of the implanted devices. Under the control of the physician, the external programmer displays the current programming parameters and permits the physician to reprogram the parameters. To this end, the physician enters appropriate commands via any of the aforementioned input devices and, under control of CPU 1602, the programming commands are converted to specific programming parameters for transmission to the implanted device 10 via telemetry wand 1628 to thereby reprogram the implanted device 10 or other devices, as appropriate.

Prior to reprogramming specific parameters, the physician may control the external programmer 1600 to display any or all of the data retrieved from the implanted device 10, from the ECG leads 1632, including displays of ECGs, IEGMs, statistical patient information (e.g., via a database or other source), diagnostic equipment 1550, etc. Any or all of the information displayed by programmer may also be printed using a printer 1636.

A wide variety of parameters may be programmed by the physician. In particular, for CRT, the AV delay and the RV-LV delay of the implanted device(s) are set to optimize cardiac function. In one example, the RV-LV delay is first set to zero while the AV delay is adjusted to achieve the best possible cardiac function (measured using any appropriate cardiac function measurement technique). Then, RV-LV delay is adjusted to achieve still further enhancements in cardiac function. With electrodes already mounted at optimal locations within the ventricles and with the AV and RV-LV delay values optimized, it is believed that the best possible cardiac function can be achieved for the patient.

Programmer 1600 optionally includes a modem to permit direct transmission of data to other programmers via the public switched telephone network (PSTN) or other interconnection line, such as a T1 line or fiber optic cable. Depending upon the implementation, the modem may be connected directly to internal bus 1604 may be connected to the internal bus via either a parallel port 1640 or a serial port 1642.

Other peripheral devices may be connected to the external programmer via the parallel port 1640, the serial port 1642, the communication interface 1645, etc. Although one of each is shown, a plurality of input output (IO) ports might be provided. A speaker 1644 is included for providing audible tones to the user, such as a warning beep in the event improper input is provided by the physician. Telemetry subsystem 1622 additionally includes an analog output circuit 1646 for controlling the transmission of analog output signals, such as IEGM signals output to an ECG machine or chart recorder.

With the programmer 1600 configured as shown, a physician or other user operating the external programmer is capable of retrieving, processing and displaying a wide range of information received from the ECG leads 1632, from the implanted device 10, the diagnostic equipment 1550, etc., and to reprogram the implanted device 10 or other implanted devices if needed. The descriptions provided herein with respect to FIG. 17 are intended merely to provide an overview of the operation of programmer and are not intended to describe in detail every feature of the hardware and software of the device and is not intended to provide an exhaustive list of the functions performed by the device.

Internal Components of Exemplary Biventricular Single Device System

For the sake of completeness, internal components of the biventricular device of FIG. 4 will now be summarized. For systems employing separate master and satellite pacemakers (such as shown in FIG. 2), selected components of the biventricular device of FIG. 4 are included either within the master device, the satellite device, or within both. Internal components of exemplary master and satellite pacing devices are set forth in the patent application referenced above entitled "Implantable Cardiac System with Master Pacing Unit and Satellite Pacing Unit".

Figure 18:
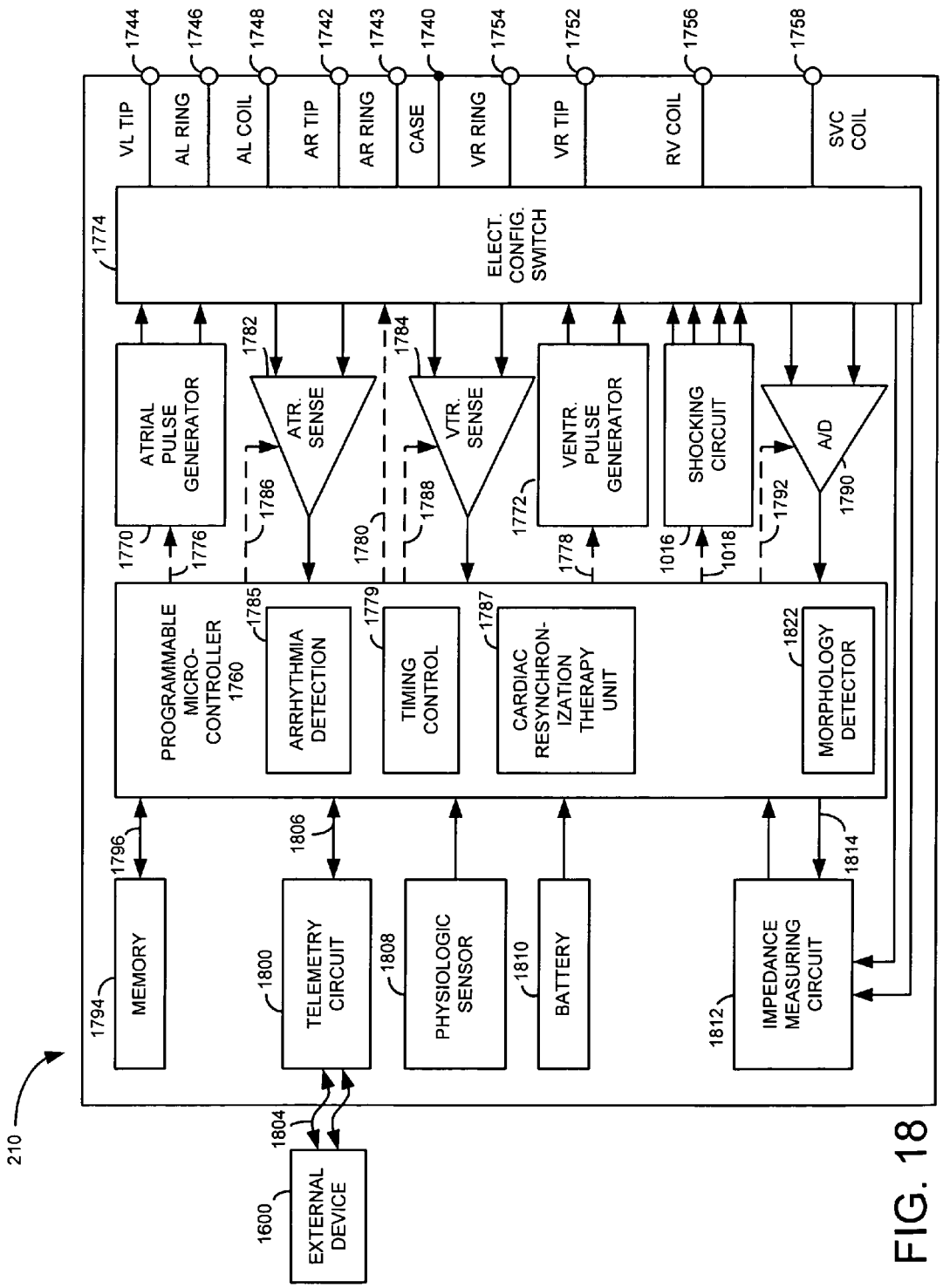
FIG. 18 is a functional block diagram of internal components of the implantable biventricular stimulation device of FIG. 4 and representative of features suitable for various other implantable devices.

Referring now to FIG. 18, pertinent components of device 210 are described. Housing 1740 (shown schematically) for the stimulation device 210 includes a connector (not shown) having an atrial tip terminal 1742 adapted for connection to the atrial tip electrode 222 and an atrial ring terminal 1743 of the atrial lead 220. The connector further includes a right ventricular tip terminal 1752, a ring ventricular ring terminal 1754, an RV shocking terminal 1756, and an SVC shocking terminal 1758 all of which are adapted for connection to the ventricular tip electrode 232, the right ventricular ring electrode 234, the RV coil electrode 236, and the SVC coil electrode 238, respectively. The housing 1740 (often referred to as the "can", "case" or "case electrode") acts as the return (common) electrode, or anode, for both the atrial tip electrode 222 and the ventricular tip electrode 232 during unipolar sensing and as the return electrode for just the ventricular tip electrode 232 during combipolar sensing. Housing 1740 can also act as the return (common) electrode, or anode, for the RV coil electrode 236, and the SVC coil electrode 238. For convenience, the names of the electrodes are shown next to the terminals. The left ventricular tip electrode 226, left atrial ring electrode 227, left atrial coil electrode 228, are adapted to be connected to the left ventricular tip terminal 1744, left atrial ring terminal 1746, and the left atrial coil terminal 1748, respectively.

At the core of the stimulation device 210 is a programmable microcontroller 1760, which controls the various modes of stimulation therapy. As is well known in the art, the microcontroller 1760 includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 1760 includes the ability to process or monitor input signals (data) as controlled by a program code stored in a designated block of memory. The details of the design and operation of the microcontroller 1760 are not critical to the present invention. Rather, any suitable microcontroller 1760 may be used that carries out the functions described herein. The use of microprocessor-based control circuits for performing timing and data analysis functions is well known in the art.

As shown in FIG. 18, an atrial pulse generator 1770 and a ventricular pulse generator 1772 generate pacing stimulation pulses for delivery by the atrial lead 220 and the ventricular lead 230, respectively, via a switch bank 1774. Ventricular pulse generator is capable of generating separate pulses for delivery to the right and left ventricles in accordance with biventricular pacing techniques. The pulse generators, 1770 and 1772, are controlled by the microcontroller 1760 via appropriate control signals, 1776 and 1778, respectively, to trigger or inhibit the stimulation pulses. The microcontroller 1760 further includes a timing control unit that controls the operation of the stimulation device timing of such stimulation pulses that is known in the art. The microcontroller 1760 may also include an AutoCapture threshold detection system or other control logic for determining whether capture has occurred and adjusting one or more parameters in response to capture or lack of capture.

The switch bank 1774 includes a plurality of switches for switchably connecting the desired electrodes to the appropriate I/O circuits, thereby providing complete electrode programmability. Accordingly, the switch bank 1774, in response to a control signal 1780 from the microcontroller 960, sets the polarity of the stimulation pulses by selectively closing the appropriate combination of switches (not shown) as is known in the art.

An atrial sense amplifier 1782 and a ventricular sense amplifier 984 are also coupled to the atrial and ventricular leads 220 and 230, respectively, through the switch bank 1774 for detecting the presence of cardiac activity. Sense amplifier 1784 is capable of separately sensing signals from both the right and left ventricles in accordance with biventricular pacing techniques. The switch bank 1774 determines the "sensing polarity" of the cardiac signal by selectively closing the appropriate switches, as is also known in the art. In this way, the clinician may program the sensing polarity independent of the stimulation polarity. The switch bank also permits the pacemaker to be set to either unipolar sensing or Combipolar sensing. For unipolar sensing, the V TIP and CASE terminals are connected to the ventricular sense amplifier for sensing a voltage differential there between and the A TIP and CASE terminals are connected to the atrial sense amplifier for sensing a voltage differential there between. For Combipolar sensing, the V TIP and CASE terminals are likewise connected to the ventricular sense amplifier but the A TIP and V TIP terminals are connected to the atrial sense amplifier for sensing a voltage differential between the tips of the atrial and ventricular leads.

Each sense amplifier, 1782 and 1784, preferably employs a low power, precision amplifier with programmable gain and/or automatic gain control, bandpass filtering, and a threshold detection circuit, known in the art, to selectively sense the cardiac signal of interest. The automatic gain control enables the device 210 to deal effectively with the difficult problem of sensing the low frequency, low amplitude signal characteristics of ventricular fibrillation. The gain control is actuated by the programmable micro controller 1760. The gains are controlled on the ventricular sense amplifier 1784 by the microcontroller using control line 1788 and on the atrial sense amplifier 1782 on control line 1786. The outputs of the atrial and ventricular sense amplifiers, 1782 and 1784, are connected to the microcontroller 1760 which, in turn, inhibits the atrial and ventricular pulse generators, 1770 and 1772, respectively, in a demand fashion whenever cardiac activity is sensed in the respective chambers.

For arrhythmia detection, the invention utilizes the atrial and ventricular sense amplifiers, 1782 and 1784, to sense cardiac signals to determine whether a rhythm is physiologic or pathologic. As used herein "sensing" is reserved for the noting of an electrical depolarization, and "detection" is the processing of these sensed depolarization signals and noting the presence of an arrhythmia. The timing intervals between sensed events (e.g., the P-P and R-R intervals) are then classified by the microcontroller 960 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, activation of special algorithms such as automatic mode switch or high atrial rate episode logging, anti-tachycardia pacing, cardioversion shocks or defibrillation shocks, also known as "tiered therapy"). An arrhythmia detection unit 985 of the microcontroller oversees arrhythmia detection. A cardiac resynchronization therapy unit 1787 oversees CRT.

Cardiac signals are also applied to the inputs of an analog to digital (ND) data acquisition system 1790. The gain of the ND converter 1790 is controlled by the microprocessor 1760 in order to match the signal amplitude and/or the resolution to a range appropriate for the function of the ND converter 1790. The data acquisition system 1790 is configured to acquire intracardiac electrogram signals (IEGMs), convert the raw analog data into a digital signal, and store the digital signals for later processing and/or telemetric transmission to an external device 1600. The data acquisition system 1790 may be coupled to the atrial and ventricular leads, 220 and 230, through the switch bank 1774 to sample cardiac signals across any pair of desired electrodes. Other connectors may exist for connection of leads or other electrodes whereby control of signals from or to or stimulation energy may be controlled via the switch bank 1774. Other electrodes optionally include electrodes for nerve or other tissue activation or sensing.

The microcontroller 1760 is further coupled to a memory 1794 by a suitable data/address bus 1796, wherein the programmable operating parameters used by the microcontroller 1760 are stored and modified, as required, in order to customize the operation of the stimulation device 210 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the heart 212 within each respective tier of therapy.

Advantageously, the operating parameters of the implantable device 210 may be non-invasively programmed into the memory 994 through a telemetry circuit 1800 in telemetric communication with an external device 1600, such as a programmer, transtelephonic transceiver, or a diagnostic system analyzer. The telemetry circuit 1800 is activated by the microcontroller 1760 by a control signal 1806. The telemetry circuit 1800 advantageously allows intracardiac electrograms and status information relating to the operation of the device 210 (as contained in the microcontroller 1760 or memory 1794) to be sent to the external device 1802 through an established communication link 1804.

In the preferred embodiment, the stimulation device 210 further includes a physiologic sensor 1808. Such sensors are commonly called "rate-responsive" sensors. The physiological sensor 1808 is used to detect the exercise state of the patient, to which the microcontroller 1760 responds by adjusting the rate and AV Delay at which the atrial and ventricular pulse generators, 1770 and 1772, generate stimulation pulses. The type of sensor used is not critical to the invention and is shown only for completeness.

The stimulation device additionally includes a battery 1810 that provides operating power to all of the circuits shown in FIG. 18. For the stimulation device 210, which employs shocking therapy, the battery must be capable of operating at low current drains for long periods of time and then be capable of providing high-current pulses (for capacitor charging) when the patient requires a shock pulse (preferably, in excess of 2 A, at voltages above 2 V, for periods of 10 seconds or more). The battery 1810 must also have a predictable discharge characteristic so that elective replacement time can be detected. Accordingly, the present invention preferably employs lithium/silver vanadium oxide batteries, as is true for most (if not all) such devices to date. As further shown in FIG. 18, the device preferably includes an impedance measuring circuit 1812, which is enabled by the microcontroller 1760 by a control signal 1822.

Depending upon the implementation, the device may function as an implantable cardioverter/defibrillator (ICD) device. That is, if it detects the occurrence of an arrhythmia, it automatically applies an appropriate electrical shock therapy to the heart aimed at terminating the detected arrhythmia. To this end, the microcontroller 1760 further controls a shocking circuit 1816 by way of a control signal 1818. The shocking circuit 1816 generates shocking pulses of low (up to about 0.5 joules), moderate (about 0.5 to 10 joules), or high energy (about 11 to 40 joules), as controlled by the microcontroller 1760. Such shocking pulses are applied to the patient's heart through at least two shocking electrodes, as shown in this embodiment, using the RV and SVC coil electrodes, 236 and 238, respectively. In alternative embodiments, the housing 1740 may act as an active electrode in combination with the RV electrode 236 alone, or as part of a split electrical vector using the SVC coil electrode 238 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia.

Defibrillation shocks are generally of moderate to high energy level (i.e., corresponding to thresholds in the range of 9 to 40 joules), delivered asynchronously (since R-waves may be too disorganized), and pertaining exclusively to the treatment of fibrillation. Accordingly, the microcontroller 1760 is capable of controlling the synchronous or asynchronous delivery of the shocking pulses.

In addition, the stimulation device may be configured to perform Automatic Mode Switching (AMS) wherein the pacemaker reverts from a tracking mode such as a VDD or DDD mode to a nontracking mode such as VVI or DDI mode. VDD, DDD, VVI and DDI are standard device codes that identify the mode of operation of the device. DDD indicates a device that senses and paces in both the atria and the ventricles and is capable of both triggering and inhibiting functions based upon events sensed in the atria and the ventricles. VDD indicates a device that sensed in both the atria and ventricles but only paces in the ventricles. A sensed event on the atrial channel triggers ventricular outputs after a programmable delay, the pacemaker equivalent of a PR interval. VVI indicates that the device is capable of pacing and sensing only in the ventricles and is only capable of inhibiting the functions based upon events sensed in the ventricles. DDI is identical to DDD except that the device is only capable of inhibiting functions based upon sensed events, rather than triggering functions. As such, the DDI mode is a non-tracking mode precluding its triggering ventricular outputs in response to sensed atrial events. Numerous other device modes of operation are possible, each represented by standard abbreviations of this type.

In general, while the subject matter has been described with reference to particular embodiments, modifications can be made thereto without departing from the spirit and scope of such subject matter.

What is claimed is:

1. A method comprising:

providing surface ECG information acquired using a multi-lead ECG system wherein each of the multi-leads has an electrode coupled to a patient;

determining conduction delay from a right ventricle to a left ventricle of the patient's heart for two or more of the multiple electrodes;

providing geometric information of the patient that correlates surface stimulation sites with corresponding sites on the patient's heart; and determining one or more stimulation sites for stimulation of the left ventricle based at least in part on the conduction delays and the geometric information.

2. The method of claim 1 wherein the geometric information comprises information for one or more fiducial markers.

3. The method of claim 2 wherein at least one of the fiducial markers marks the position of a lead of the multi-lead ECG system.

4. The method of claim 1 wherein the determining one or more stimulation sites for cardiac resynchronization therapy.

5. The method of claim 1 wherein the determining one or more stimulation sites further comprises analyzing a plurality of ST segments of the surface ECG information to determine the one or more stimulation sites.

6. The method of claim 1 wherein the geometric information comprises information for one or more epicardial veins.

7. The method of claim 6 wherein the one or more epicardial veins comprises an epicardial vein suitable for positioning an electrode for stimulation of the left ventricle.

8. The method of claim 1 wherein the geometric information comprises 3-D information.

9. The method of claim 1 wherein the determining determines cardiac characteristics responsible for generating the ECG information.

10. The method of claim 1 wherein the determining determines a solution to an inverse problem.

11. The method of claim 1 wherein the determining determines the one or more stimulation sites based on site limitations.

12. The method of claim 1 further comprising associating the ECG information with the geometric information.

13. The method of claim 1 wherein the geometric information comprises 3-D information for the heart.

14. The method of claim 1 wherein the geometric information comprises 3-D information for the torso.

15. The method of claim 1 wherein the geometric information comprises 3-D information to locate the heart within the torso.

16. The method of claim 1 wherein the geometric information comprises 3-D information of the outer surface of the torso.

17. An apparatus comprising:

an input for receipt of surface ECG information acquired using a multi-lead ECG system;

an input for geometric information acquired using magnetic resonance, x-rays or ultrasound that correlates surface stimulation sites with corresponding sites on the patient's heart;

a processor configured to determine a conduction delay from a right ventricle to a left ventricle of the patient's heart for two or more of the multiple electrodes; and control logic operable in conjunction with the processor to determine one or more stimulation sites for the left ventricle based at least in part on the conduction delays and received geometric information.

18. The apparatus of claim 17 further comprising a circuit for communicating with an implantable device.

19. The apparatus of claim 17 further comprising control logic to associate geometric information for one or more fiducial markers with locations of one or more leads of the multi-lead ECG system as located for acquisition of the surface ECG information.

20. A system comprising:

means for acquiring surface ECG information;

means for acquiring geometric information of a patient that correlates surface stimulation sites with corresponding sites on the patient's heart;

means for determining a conduction delay from a right ventricle to a left ventricle of the patient's heart for two or more of the multiple electrodes; and means for determining one or more stimulation sites for stimulation of the left ventricle based at least in part on the ECG information and the geometric information.

* * * * *